US010918532B2

(12) United States Patent
Schneider et al.

(10) Patent No.: US 10,918,532 B2
(45) Date of Patent: Feb. 16, 2021

(54) METHODS OF MAKING ELASTIC BELTS FOR ABSORBENT ARTICLES

(71) Applicant: The Procter & Gamble Company, Cincinnati, OH (US)

(72) Inventors: Uwe Schneider, Cincinnati, OH (US); Farihah Ibrahim, Cincinnati, OH (US); Nicholas Goyette, Cincinnati, OH (US); Masaharu Nishikawa, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/208,810

(22) Filed: Dec. 4, 2018

(65) Prior Publication Data

US 2019/0183689 A1 Jun. 20, 2019

Related U.S. Application Data

(60) Provisional application No. 62/607,489, filed on Dec. 19, 2017.

(51) Int. Cl.
*A61F 13/49* (2006.01)
*A61F 13/511* (2006.01)
(Continued)

(52) U.S. Cl.
CPC .. *A61F 13/49011* (2013.01); *A61F 13/15593* (2013.01); *A61F 13/15707* (2013.01);
(Continued)

(58) Field of Classification Search
CPC .......... A61F 13/49011; A61F 13/51104; A61F 13/512; A61F 13/15707; B26F 1/00; B32B 38/0004; B32B 38/0012; Y10T 156/1057
See application file for complete search history.

(56) References Cited

U.S. PATENT DOCUMENTS 4,614,679 A * 9/1986 Farrington, Jr. ...... A47L 23/266
428/138
5,667,619 A 9/1997 Alikhan
(Continued)

FOREIGN PATENT DOCUMENTS

CN 1197538 C 4/2005
CN 101152114 4/2008
(Continued)

OTHER PUBLICATIONS

All Office Actions, U.S. Appl. No. 15/893,730.
(Continued)

*Primary Examiner* — Mark A Osele
*Assistant Examiner* — Christopher C Caillouet
(74) *Attorney, Agent, or Firm* — Christian M. Best

(57) ABSTRACT

The present disclosure is directed to methods of manufacturing elastic belts for absorbent articles. The elastic belts may be used as waist bands, or portions thereof, in absorbent articles. The elastic belts may define a first nonwoven substrate, a second nonwoven substrate, and a plurality of elastic strands positioned intermediate the first and second nonwoven substrates. The elastic belts may define a plurality of apertures therethrough to create breathability in the elastic belts.

5 Claims, 33 Drawing Sheets

(51) Int. Cl.
*B32B 38/00* (2006.01)
*A61F 13/512* (2006.01)
*A61F 13/496* (2006.01)
*A61F 13/15* (2006.01)
*B29C 53/24* (2006.01)
*B26F 1/00* (2006.01)
*D04H 1/70* (2012.01)
*D04H 11/08* (2006.01)
*B29L 31/48* (2006.01)

(52) U.S. Cl.
CPC ...... *A61F 13/15723* (2013.01); *A61F 13/496* (2013.01); *A61F 13/512* (2013.01); *A61F 13/5116* (2013.01); *A61F 13/51104* (2013.01); *B26F 1/00* (2013.01); *B29C 53/24* (2013.01); *B29L 2031/4878* (2013.01); *D04H 1/70* (2013.01); *D04H 11/08* (2013.01); *Y10T 156/1057* (2015.01)

(56) References Cited

U.S. PATENT DOCUMENTS

| | | | |
|---|---|---|---|
| 6,274,218 | B1 | 8/2001 | Shimizu |
| 7,534,928 | B2 | 5/2009 | Sakamoto et al. |
| 7,569,264 | B2 | 8/2009 | Toyoshima et al. |
| 7,971,526 | B2 | 7/2011 | Blenke et al. |
| 8,221,370 | B2 | 7/2012 | Cohen et al. |
| 8,450,557 | B2 | 5/2013 | Nishitani et al. |
| 9,108,355 | B2 | 8/2015 | Kume et al. |
| 9,532,908 | B2 * | 1/2017 | Wade ............... A61F 13/49012 |
| 10,603,229 | B2 | 3/2020 | Trinkaus et al. |
| 2001/0036786 | A1 | 11/2001 | Heden et al. |
| 2002/0016122 | A1 | 2/2002 | Curro et al. |
| 2003/0121380 | A1 * | 7/2003 | Cowell ............. A61F 13/15707 83/30 |
| 2003/0187418 | A1 | 10/2003 | Kudo et al. |
| 2006/0003657 | A1 | 1/2006 | Larson et al. |
| 2006/0144503 | A1 | 7/2006 | Carr |
| 2006/0243367 | A1 | 11/2006 | Engelhart et al. |
| 2008/0221543 | A1 | 9/2008 | Wilkes et al. |
| 2008/0260996 | A1 | 10/2008 | Heilman et al. |
| 2008/0294135 | A1 | 11/2008 | Hara et al. |
| 2010/0286646 | A1 * | 11/2010 | Takino ................. A61F 13/539 604/385.3 |
| 2012/0064298 | A1 | 3/2012 | Orr et al. |
| 2012/0238978 | A1 | 9/2012 | Weisman et al. |
| 2012/0276341 | A1 | 11/2012 | Lake et al. |
| 2014/0023822 | A1 | 1/2014 | Tai et al. |
| 2014/0080692 | A1 | 3/2014 | Lenser et al. |
| 2014/0296815 | A1 | 10/2014 | Takken et al. |
| 2014/0324009 | A1 | 10/2014 | Lee et al. |
| 2015/0164705 | A1 | 6/2015 | Thomas et al. |
| 2015/0290050 | A1 * | 10/2015 | Wada ..................... B32B 5/022 604/385.01 |
| 2015/0351973 | A1 | 12/2015 | Tsujimoto et al. |
| 2016/0136003 | A1 | 5/2016 | Mullane et al. |
| 2016/0235590 | A1 | 8/2016 | Coe et al. |
| 2016/0235592 | A1 | 8/2016 | Coe et al. |
| 2016/0354254 | A1 | 12/2016 | Eimann et al. |
| 2017/0014281 | A1 | 1/2017 | Xie et al. |
| 2018/0000656 | A1 | 1/2018 | Roe et al. |
| 2018/0228667 | A1 | 8/2018 | Schneider et al. |

FOREIGN PATENT DOCUMENTS

| | | |
|---|---|---|
| CN | 202069775 U | 12/2011 |
| CN | 202096358 U | 1/2012 |
| CN | 202515887 U | 11/2012 |
| CN | 202644115 U | 1/2013 |
| CN | 202982411 U | 6/2013 |
| CN | 204237074 U | 4/2015 |
| CN | 204798134 U | 11/2015 |
| CN | 103339309 B | 6/2016 |
| JP | H05228173 | 9/1993 |
| JP | 3748763 B | 2/2006 |
| JP | 2009153879 | 7/2009 |
| JP | 2010133071 | 6/2010 |
| JP | 2011132623 | 7/2011 |
| JP | 5021719 B | 9/2012 |
| JP | 5103100 B | 12/2012 |
| JP | 201425187 A | 2/2014 |
| JP | 5674454 B | 2/2015 |
| JP | 5674455 B | 2/2015 |
| JP | 5764323 B | 8/2015 |
| JP | 5858776 B | 2/2016 |
| JP | 5921866 B | 5/2016 |
| JP | 5985258 B | 9/2016 |
| JP | 2009153879 | 7/2019 |
| WO | WO2003015681 A1 | 2/2003 |
| WO | WO2015098373 | 7/2015 |
| WO | WO2016040104 | 3/2016 |
| WO | WO2018020677 | 2/2018 |

OTHER PUBLICATIONS

All Office Actions, U.S. Appl. No. 15/893,727.
All Office Actions, U.S. Appl. No. 15/893,740.
International Search Report and Written Opinion, PCT/US2018/064152, dated Mar. 18, 2019.
All Office Actions, U.S. Appl. No. 16/791,386.
All Office Actions, U.S. Appl. No. 15/893,735.
All Office Actions, U.S. Appl. No. 15/893,835.

* cited by examiner

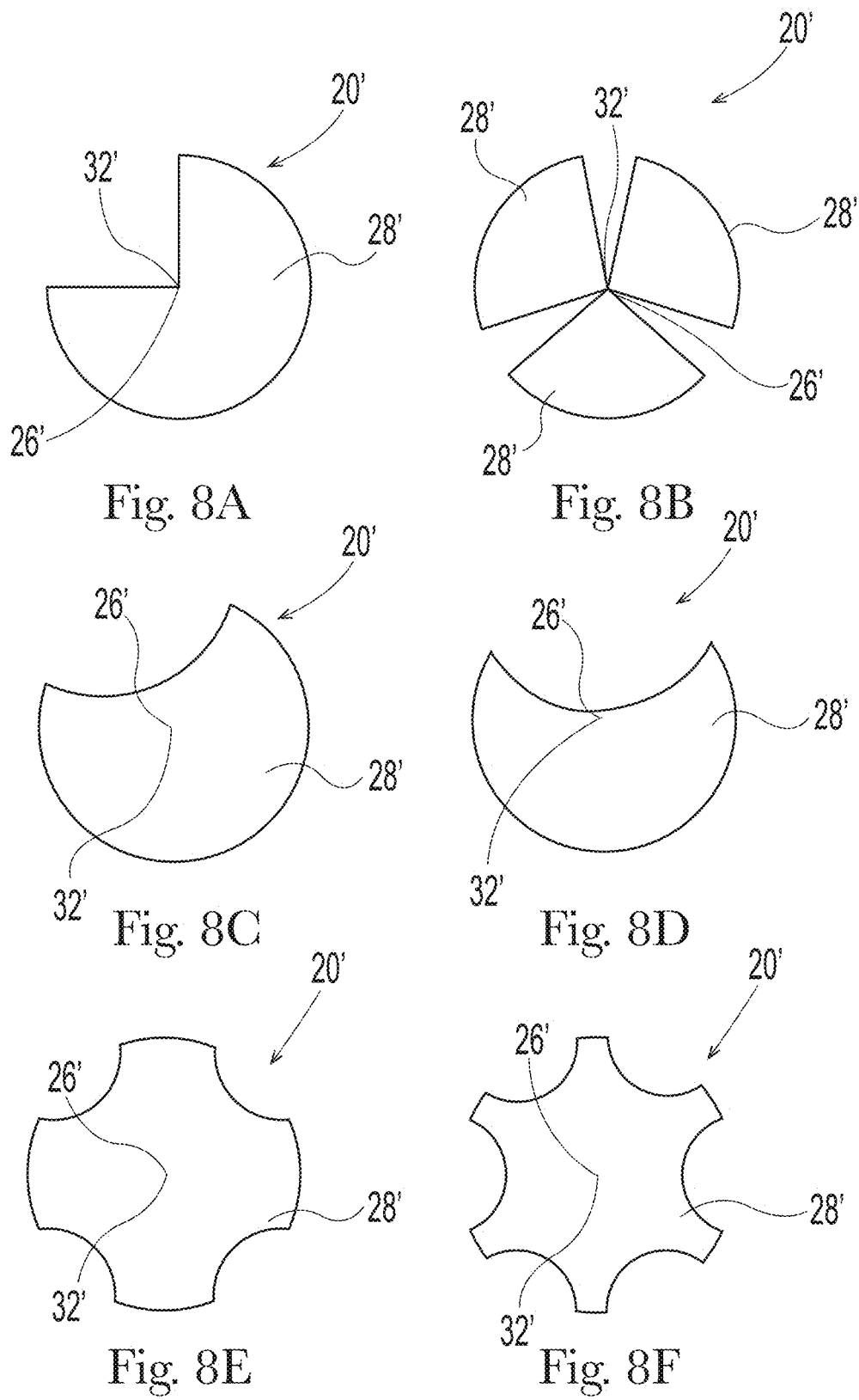

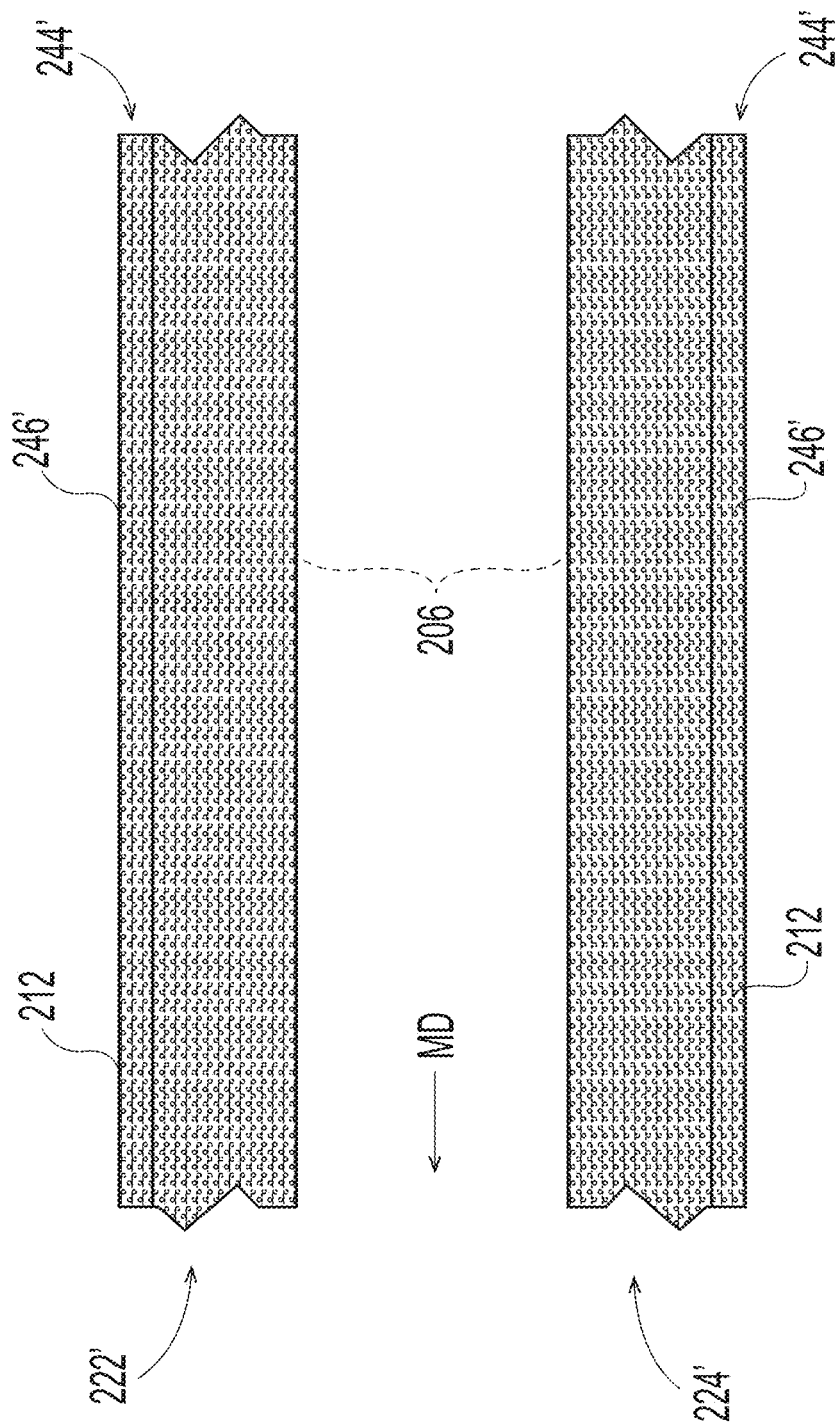

METHODS OF MAKING ELASTIC BELTS FOR ABSORBENT ARTICLES

CROSS REFERENCE TO RELATED APPLICATION

This application claims the benefit, under 35 U.S.C. § 119(e), to U.S. Provisional Patent Application No. 62/607,489, filed on Dec. 19, 2017, which is hereby incorporated by reference in its entirety.

FIELD

The present disclosure is generally directed to methods of making elastic belts for absorbent articles. The present disclosure is more specifically directed to methods of making apertured elastic belts for absorbent articles.

BACKGROUND

Absorbent articles, such as taped diapers, pants, and adult incontinence articles, for example, are designed to contain and absorb bodily exudates (i.e., urine, bowel movements, and menses). These absorbent articles frequently have waist bands that fasten around the waist of a wearer to maintain the absorbent article in position on a wearer. A single waist band may be separated into a front waist band and a rear waist band. In some instances, the waist band may be continuous (i.e., have permanent side seams between the front and rear waist bands) such that the absorbent article is pulled up the legs, over the buttocks and hips, and positioned around the waist. In other instances, the waist band may be refastenable (i.e., have refastenable side seams between the front and rear waist bands) such that the absorbent article may be applied like a taped diaper and then the front and rear waist bands may be attached to each other at the side seams or otherwise. In some instances, absorbent articles with refastenable waist bands may be supplied with the waist bands fastened and be applied like absorbent articles having continuous waist bands. The waist bands may comprise elastic laminates or belts that typically comprise two or more nonwoven materials and a plurality of elastic strands disposed between at least two of the nonwoven materials. One issue with manufacturing waist bands is to process them without breaking the elastic strands. At times, methods of processing the waist bands, such as aperturing and/or creating three-dimensional elements in the waist bands, may break or snap the elastic strands. Waist band processing methods need to be improved to eliminate, or at least reduce, elastic strand breakage.

SUMMARY

The methods of making elastic belts or waist bands for absorbent articles of the present disclosure solve the above-mentioned problems of waist band processing without causing elastic strand breakage or with reduced elastic strand breakage. The methods of the present disclosure also allow apertures and/or three dimensional elements to be made in the elastic belts, with at least reduced elastic strand breakage, either during absorbent article manufacturing or prior to absorbent article manufacturing (i.e., during elastic belt making). The elastic strands of the present disclosure may comprise multi-filament strands. In such an instance, when a point of an aperturing pin contacts an elastic strand, the point may push the elastic strand to one side or the other or it may force some of the filaments to one side of the pin and others of the filaments to another side of the pin. The point may also break some of the filaments, while other filaments and the elastic strand overall remain in-tact and functional. This reduces and/or eliminates elastic strand breakage. In some instances, the elastic strands may comprise multi-filament elastic strands.

BRIEF DESCRIPTION OF THE DRAWINGS

While the specification concludes with claims particularly pointing out and distinctly claiming the subject matter which is regarded as forming the present invention, it is believed that the present disclosure will be better understood from the following description which is taken in conjunction with the accompanying drawings in which the designations are used to designate substantially identical elements and in which:

FIG. 8A-8F are example top views of portions of projections of the first roll;

FIG. 24A is a top view of two elastic belts having apertures and/or three-dimensional elements being conveyed in a machine direction;

DETAILED DESCRIPTION

Various non-limiting forms of the present disclosure will now be described to provide an overall understanding of the principles of the structure, function, manufacture, and use of the methods of making elastic belts for absorbent articles disclosed herein. One or more examples of these non-limiting forms are illustrated in the accompanying drawings. Those of ordinary skill in the art will understand that the methods of making elastic belts for absorbent articles specifically described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

Initially, example tooling that may be used in the methods of making elastic belts for absorbent articles will be described. As will be described further herein, the elastic belts may comprise a first nonwoven substrate, a second nonwoven substrate, and a plurality of elastic strands positioned intermediate the first and second nonwoven substrates. In some instances, the elastic belts may comprise more than two nonwoven substrates for softness, athletics, and/or other purposes.

Tooling

Figure 1:
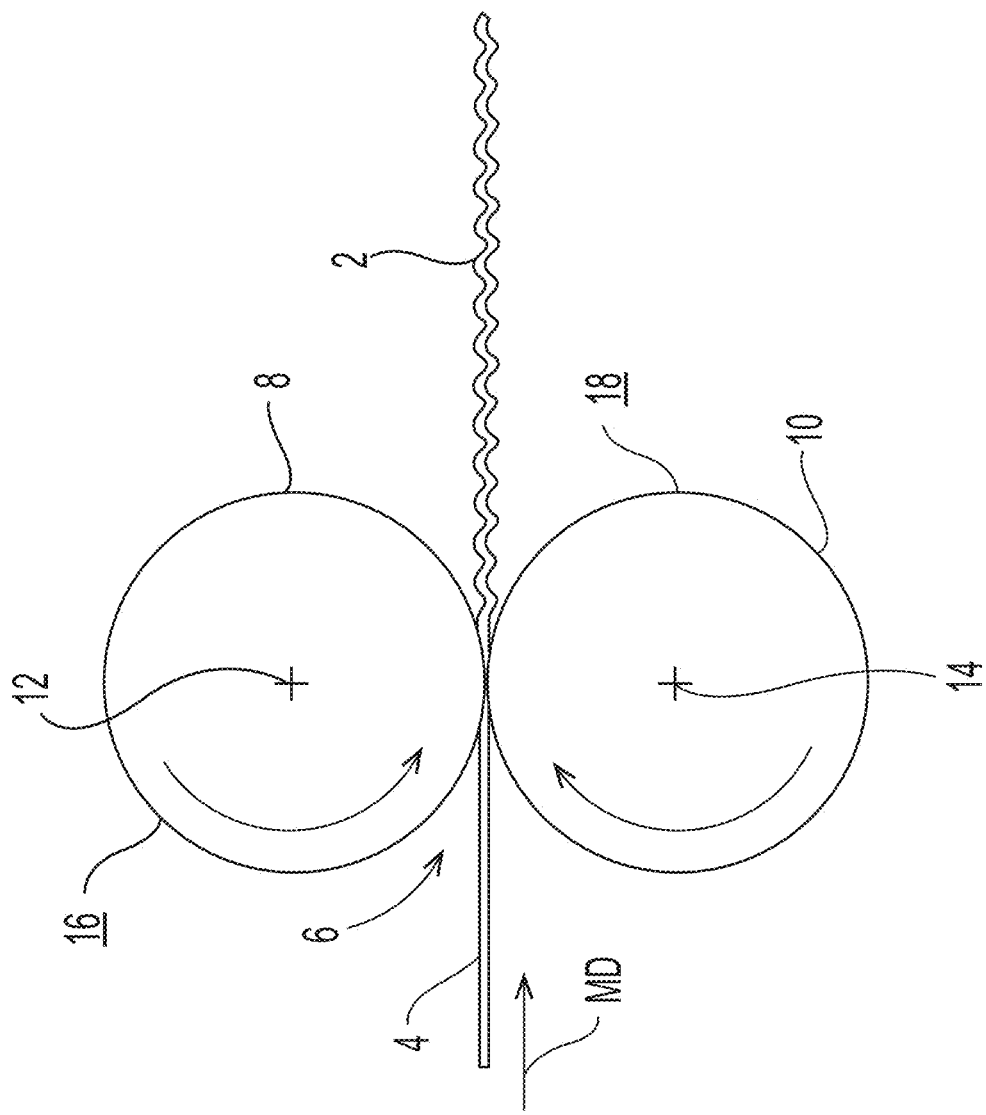
FIG. 1 is a view of a pair of rolls having a substrate conveyed therebetween.

Referring to FIG. 1, the tooling to create three-dimensional, apertured elastic belts will be discussed first. Modifications of such tooling may be used to create three-dimensional elastic belts without apertures and/or apertured elastic belts without separately formed three-dimensional elements. When only apertures are formed by the tooling, three-dimensionality may be imparted by the elastic strands in the elastic belts. Such modifications to the tooling will be discussed subsequently.

The tooling will initially be explained with application to a single nonwoven material for ease in description and illustration, although the process will be the same or similar for elastic belts.

A three-dimensional, apertured substrate 2 may be created by conveying a precursor substrate 4 through a nip 6 formed between a first roll 8 and a second roll 10. At least portions of the first roll 8 may be intermeshingly engaged with at least portions of the second roll 10. Portions of the first and second rolls that are not in intermeshing contact may be in rolling contact or not in contact at all. Details of the first and second rolls 8, 10 will be illustrated in later figures. The precursor substrate 4, the first roll 8, the second roll 10, and/or the three-dimensional substrate or three-dimensional apertured formed substrate 2 may be heated to promote better retention of three-dimensional elements in the formed substrate 2 and allow easier formation of three-dimensional elements and apertures.

Referring again to FIG. 1, the first and second rolls 8 and 10 may be configured to create only three-dimensional elements in the precursor substrate 4, only apertures in the precursor substrate 4, or may be configured to create three-dimensional elements and apertures in the precursor substrate 4 to form a three-dimensional, apertured formed substrate 2. The first roll 8 may rotate about a first rotational axis 12 in the direction indicated by the arrow on the first roll 8 and the second roll 10 may rotate about a second rotational axis 14 in the direction indicated by the arrow on the second roll 10. In other instances, the first roll 8 may rotate in the opposite direction as the arrow on the first roll 8 and the second roll 10 may rotate in the opposite direction as the arrow on the second roll 10, for example. The first roll 8 may comprise a first radial outer surface 16 and the second roll 10 may comprise a second radial outer surface 18. The first rotational axis 12 and the second rotational axis 14 may be positioned generally parallel to each other to form a nip 6 between the first and second rolls 8, 10. The precursor substrate 4 may be conveyed in a machine direction (arrow MD) on an absorbent article manufacturing line through the nip 6.

Figure 2:
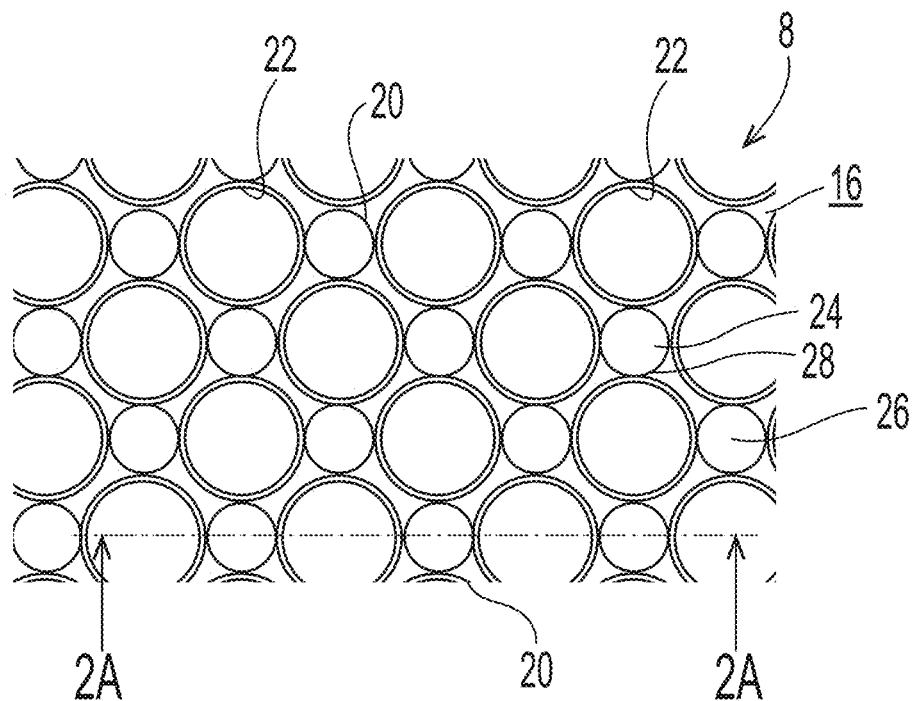
FIG. 2 is a top view of an example portion of a first roll of the pair of rolls of FIG. 1.
Figure 2A:
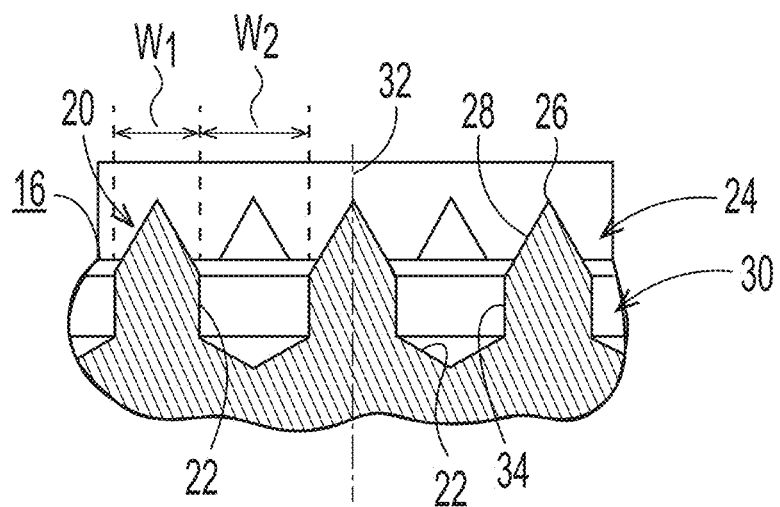
FIG. 2A is a cross-sectional view of the first roll taken about line 2A-2A of FIG. 2.

FIG. 2 is a front view of a portion of an example of the first roll 8. FIG. 2A is a cross-sectional view of FIG. 2 taken about line 2A-2A. The first roll 8 may comprise a first plurality of projections 20 extending at least partially outwardly from the first radial outer surface 16. The first plurality of projections 20 may be configured to form, or at least partially form apertures in the precursor substrate 4. In some instances, distal ends of the projections 20 may be rounded to merely form three-dimensional elements in the precursor substrate 4 instead of apertures. The first roll 8 may also comprise a first plurality of recesses 22 defined in the first radial outer surface 16. At least some of, most of, or all of the first plurality of projections 20 may comprise first distal portions 24 comprising elongated aperturing structures. First distal ends 26 of the first distal portions 24 may form a point. The term "point" as used herein may be at least partially rounded off, but still capable of puncturing a precursor substrate. The term "point" also includes a configuration where pins extend from the distal ends, wherein the pins create the apertures. The first distal portions 24 may comprise one or more side walls 28. At least some of, most of, or all of the first plurality of projections 20 may each comprise a first base 30. The first plurality of projections 20 may comprise a central longitudinal axis 32 that intersects the point or first distal end 26. The base 30 may comprise side walls 34 that may extend parallel to, or substantially parallel to, the first central longitudinal axis 32. In other instances, the side walls 34 may extend within +/−25 degrees of the first central longitudinal axis 32. The side walls 34, in some instances, may also be arcuate or have arcuate portions.

Still referring to FIGS. 2 and 2A, the first distal portions 24 may form cones or conical structures. In such instances, the first distal portions 24 may have a single side wall 28 that surrounds the first central longitudinal axis 32. In other instances, the first distal portions 24 may form other polygonal shapes where two or more side walls 28 are formed. As an example, the first distal portions 24 may form tetrahedron structures with three separate side walls. In either instance, the side wall or side walls 28 may not be fully continuous around the first central longitudinal axis 32 as will be explained in further detail below. The side wall or walls 28, whether continuous or discontinuous, may have a first angle in the range of about 20 degrees to about 80 degrees, about 30 degrees to about 70 degrees, about 35 degrees to about 65 degrees, about 40 degrees to about 60 degrees, about 40 degrees to about 55 degrees, or about 40 degrees to about 50 degrees, relative to the first central longitudinal axis 32, specially reciting all 0.1 degree increments within the specified ranges and all ranges formed therein or thereby. Referring to FIG. 2, at least some of the projections of first plurality of projections 20 may be surrounded by four recesses of the first plurality of recesses 22, for example. Again referring to FIG. 2, at least some of the recesses of the first plurality of recesses 22 may be surrounded by four projections of the first plurality of projections 20, for example.

Referring to FIG. 2A, at least some of, or all of, the bases 30 of the first plurality of projections 20 may have a first width, W1, taken in a direction generally parallel to the first rotational axis 12 (or perpendicular to the first central longitudinal axis 32). At least some of the recesses 22 in areas adjacent to the bases 30 may have a second width, W2, taken in a direction generally parallel to the first rotational axis 12. The first width, W1, may be the same as, different than, smaller than, or greater than the second width, W2.

Figure 3:
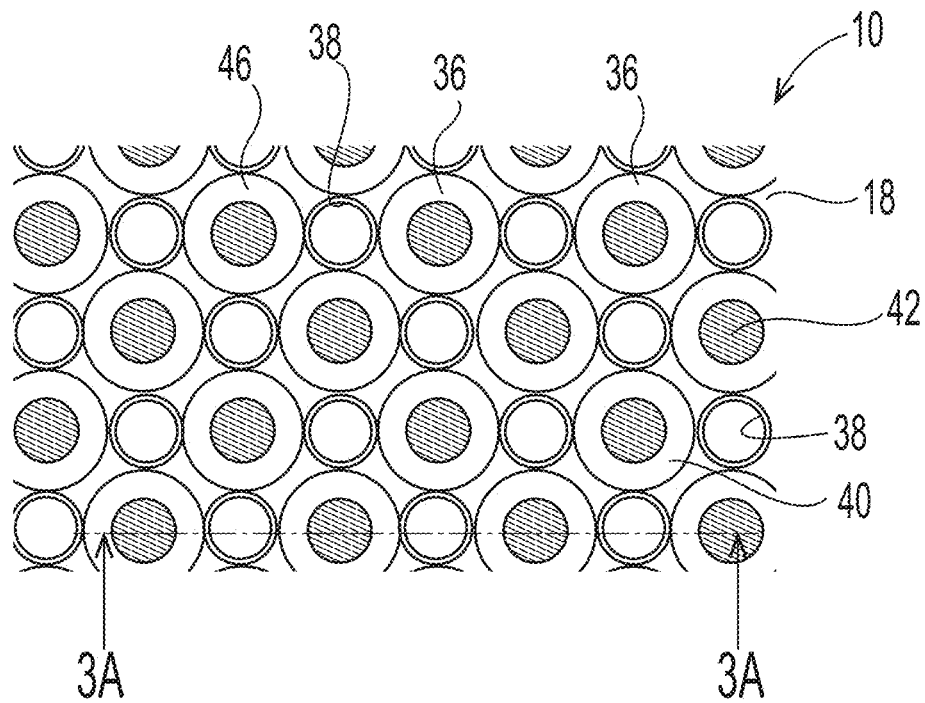
FIG. 3 is a top view of an example portion of a second roll of the pair of rolls of FIG. 1.
Figure 3A:
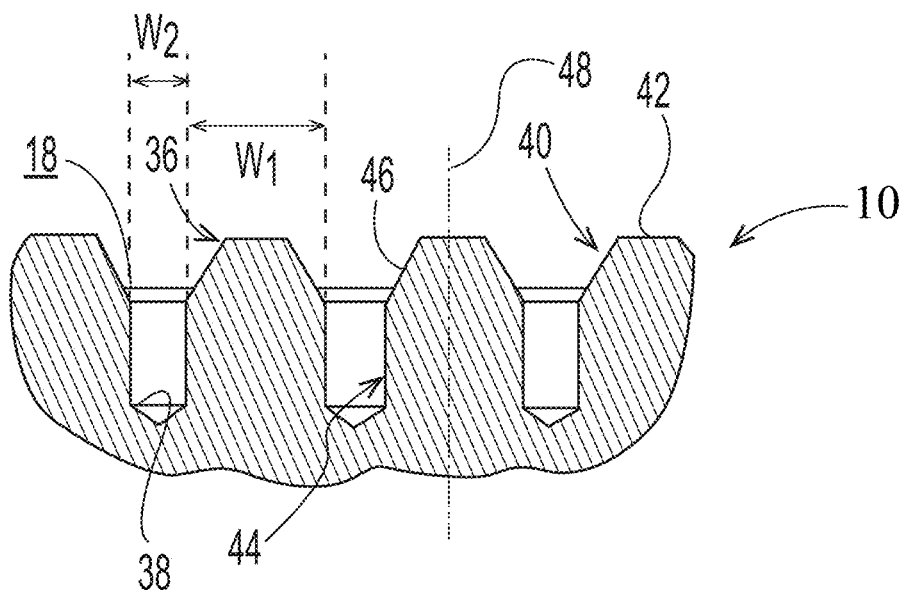
FIG. 3A is a cross-sectional view of the second roll taken about line 3A-3A of FIG. 3.

FIG. 3 is a front view of a portion of an example of the second roll 10. FIG. 3A is a cross-sectional view of FIG. 3 taken about line 3A-3A. The second roll 10 may comprise a second plurality of projections 36 extending at least partially outwardly from the second radial outer surface 18. The second plurality of projections 36 are configured to form three-dimensional elements in the precursor substrate 4. The second plurality of projections 36 have a second plurality of recesses 38 defined in the second radial outer surface 18. At least some of, most of, or all of the second plurality of projections 36 comprise second distal portions 40 and second distal ends 42. The second plurality of projections 36 comprise bases 44. At least some of, most of, or all of the second plurality of projections 36 each comprise shoulders 46 positioned intermediate the bases 44 and the second distal ends 42. The second plurality of projections 36 each comprise a central longitudinal axis 48 extending in a direction generally perpendicular to the second rotation axis 14. The shoulders 46 may have a second angle relative to the second central longitudinal axis 48 in the range of about 20 degrees to about 80 degrees, about 30 degrees to about 70 degrees, about 35 degrees to about 65 degrees, about 40 degrees to about 60 degrees, about 40 degrees to about 55 degrees, or about 40 degrees to about 50 degrees, relative to the second central longitudinal axis 48, specially reciting all 0.1 degree increments within the specified ranges and all ranges formed therein or thereby. The first angle of the first distal portions 24 may be the same as or different than the second angle of the shoulders 46. As an example, the first angle may be within about +/−0.01 degrees to about 15 degrees, or within about +/−0.01 degrees to about 10 degrees, of the second angle, specifically including all 0.001 degree increments within the specified ranges and all ranges formed therein or thereby. As further examples, the first angle may be with +/−15, 14, 13, 12, 11, 10, 9, 8, 6, 5, 4, 3, 2, 1.5, 1, 0.75, 0.5, 0.25, or 0.1 degrees of the second angle. As yet another example, the first angle may be substantially the same as (e.g., +/−0.5 degrees), or the same as, the second angle. The purpose of having the first and second angles the same, substantially the same, or relatively close to each other is to create a compressed region or densified area at least partially, or fully, surrounding a portion of three-dimensional elements (or surrounding or partially surrounding the apertures) in the precursor substrate 4. These compressed regions or densified areas help resist compression (such as from packaging) and help maintain the three-dimensional elements. The compressed regions may be formed on portions of the three-dimensional elements and/or may at least partially surround perimeters of the apertures to stabilize the three-dimensional elements and/or the apertures when made at line speed. The compressed regions or densified areas are not merely primary fiber bonds used in the formation of a nonwoven substrate (i.e., bonds used to hold the fibers together).

Referring to FIG. 3, at least some of the projections of second plurality of projections 36 may be surrounded by four recesses of the second plurality of recesses 38. Again referring to FIG. 3, at least some of the recesses of the second plurality of recesses 38 may be surrounded by four projections of the second plurality of projections 36.

Referring to FIG. 3A, at least some of, or all of, the bases 44 of the second plurality of projections 36 may have a first width, W3, in a direction generally parallel to the second rotational axis 14. At least some of the recesses 38 in areas adjacent to the bases 44 may have a second width, W4, in a direction generally parallel to the second rotational axis 14. The first width, W1, may be the same as, different than, smaller than, or greater than the second width, W2.

Figure 4:
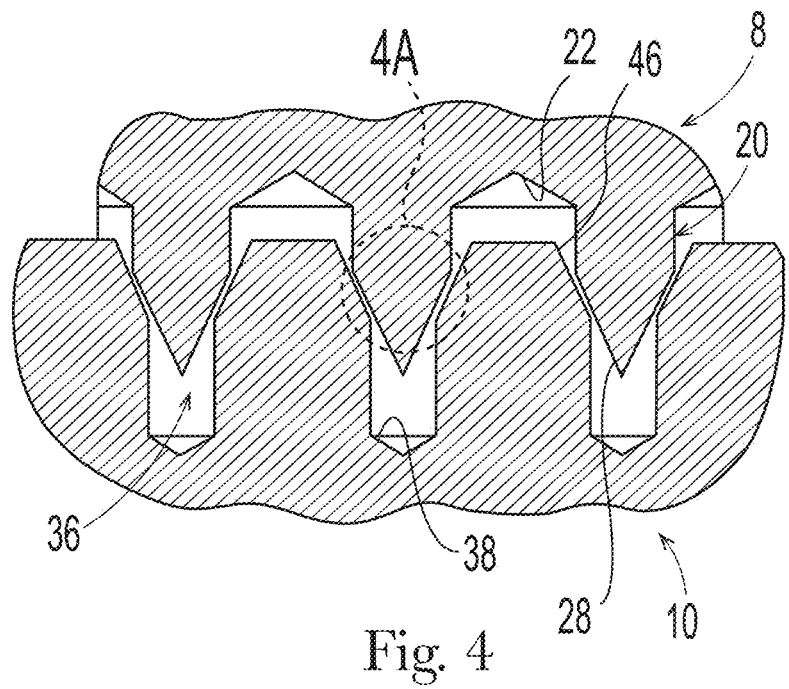
FIG. 4 is a simplified schematic cross-sectional illustration of the portion of the first roll of FIG. 2A intermeshed with the portion of the second roll of FIG. 3A.

FIG. 4 is a simplified schematic cross-sectional illustration of the portion of the first roll 8 of FIG. 2A intermeshed with the portion of the second roll 10 of FIG. 3A. The remainder of the outer surface of the first roll 8 having the first plurality of projections 20 and the first plurality of recesses 22 and the remainder of the second roll 10 having the second plurality of projections 36 and the second plurality of recesses 38 will, in most instances, intermesh in the same fashion, if desired. In some instances, it may be desirable to only create three-dimensional elements and apertures in a central longitudinal strip, as will be discussed in more detail below. The precursor substrate 4 is not illustrated in FIG. 4 for clarity in illustration of the tooling, but would be present in the gap between the two rolls 8, 10. In FIG. 4, portions of the first plurality of projections 20 of the first roll 8 are intermeshed with portions of the second plurality of recesses 38 in the second roll 10. Also, portions of the second plurality of projections 36 of the second roll 10 are intermeshed with portions of the first plurality of recesses 22 of the first roll 8. In such a fashion, portions of one or more side walls 28 of the first distal portions 24 are brought into close proximity to portions of the shoulders 46 of the second distal portions 40. The side walls 28 and the shoulders 46 together may apply a force to the precursor substrate 4 to compress the precursor substrate 4 therebetween. When the precursor substrate 4 is positioned in the nip between the first roll 8 and the second roll 8, the shoulders 46 and portions of the one or more side walls 28 may be used to create compressed regions or densified areas in the precursor substrate 4. The compressed regions or densified areas in the substrate may aid in resisting compression of three-dimensional elements. The compression may be classified as reversible elastic deformation of the precursor substrate 4 (e.g., a nonwoven material). Compression means squeezing air out of a lofty precursor substrate and causing straightening and/or nesting of the fibers of the precursor substrate. Compression does not mean causing, for example, polymer in a nonwoven material to begin flowing to fill the air voids and then solidifying (known as non-reversible elastic deformation). Non-reversible elastic deformation may create rigid areas in the precursor substrate, thereby reducing the precursor substrates' softness. Thus, reversible elastic deformation is more desirable than non-reversible elastic deformation in that it provides better softness while still providing resistance to compression of the three-dimensional elements. Thus, a gap, G, is provided between the side walls 28 and the shoulders 46 to only allow for compression of the precursor substrate therebetween without causing it to melt and solidify.

Figure 4A:
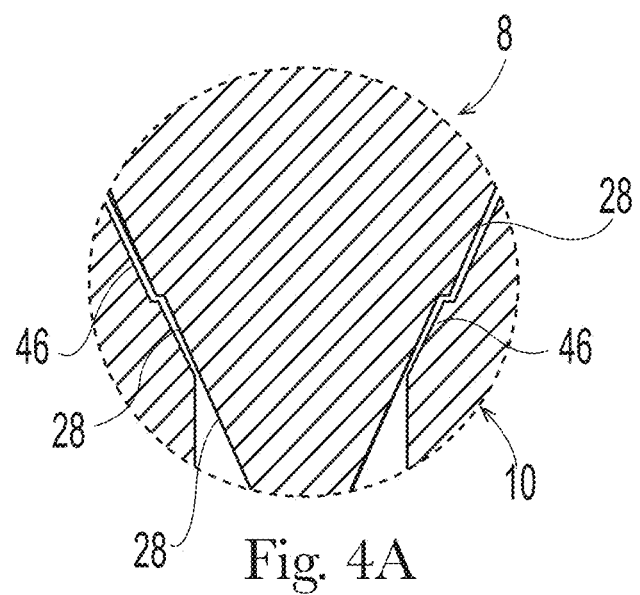
FIG. 4A is an exploded view of region 4A in FIG. 4.

FIG. 4A is an exploded view of region 4A of FIG. 4. FIG. 4A illustrates an example, optional configuration for the shoulders 46 and the side walls 28, wherein the shoulders 46 and the side walls 28 each have two off-set surfaces. Any of the shoulders 46 and the side walls 28 disclosed herein may have such off-set surfaces. In other instances, the shoulders 46 and the side walls 28 may not have two off-set surfaces.

The first plurality of projections 20 may not fully engage the second plurality of the recesses 38 and the second plurality of projections 36 may not fully engage the first plurality of the recesses 22. As stated above, the first plurality of projections 20, namely the points and the first distal portions 24, in combination with the second plurality of recesses 38, are used to form apertures in the precursor substrate 4. The second plurality of projections 36, namely the second distal ends 42 and the second distal portions 40, in combination with the first plurality of recesses 22 are used to form three-dimensional elements in the precursor substrate 4. The compressed regions may be formed in the three-dimensional elements to aid the three-dimensional elements to resist compression, such as compression caused by packaging.

Figure 5:
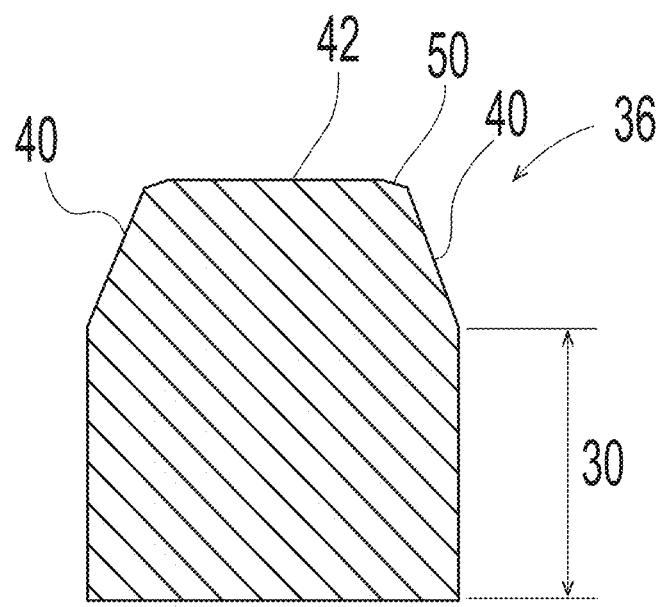
FIG. 5 is a cross-sectional view of a portion of an example projection of the second roll.
Figure 6:
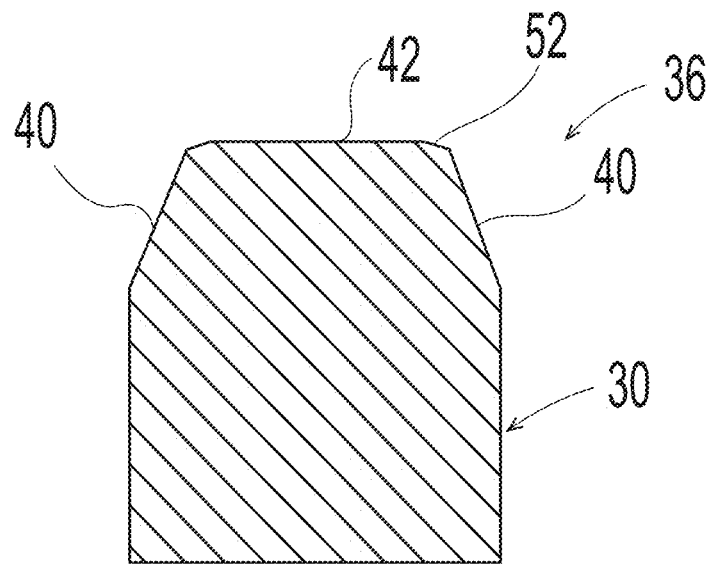
FIG. 6 is another cross-sectional view of a portion of an example projection of the second roll.

Referring to FIG. 5, at least some of the second plurality of projections 36 may have beveled portions 50 intermediate the second distal ends 42 and the second distal portions 40. This prevents, or at least inhibits, the precursor substrate 4 from contacting a sharp corner and tearing or creating a sharp edge in the precursor substrate 4. Referring to FIG. 6, at least some of the second plurality of projections 36 may have rounded corners 52 intermediate the second distal ends 42 and the second distal portions 40. This prevents, or at least inhibits, the precursor substrate 4 from contacting a sharp corner and tearing or creating a sharp edge in the precursor substrate 4.

Figure 7A:
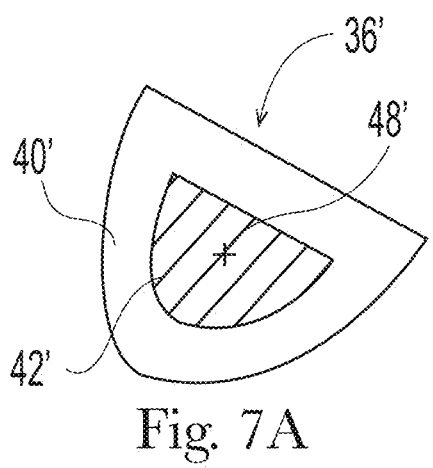
FIGS. 7A-7G are example top views of portions of distal ends of projections of the second roll.
Figure 7B:
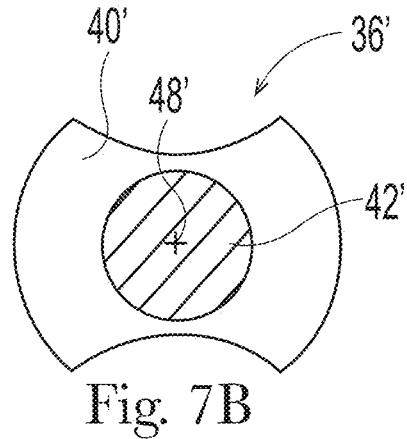
Figure 7C:
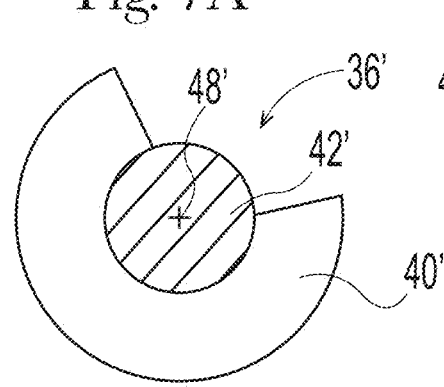
Figure 7D:
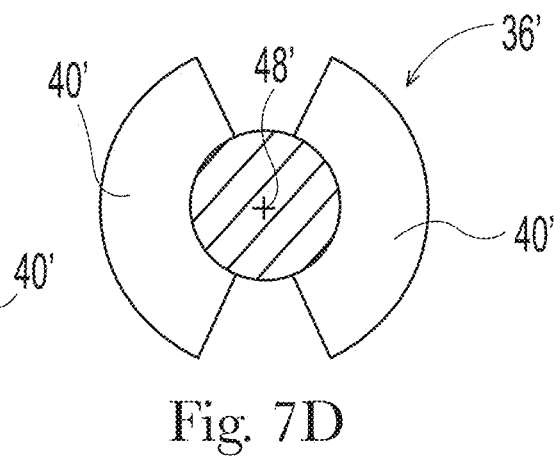
Figure 7E:
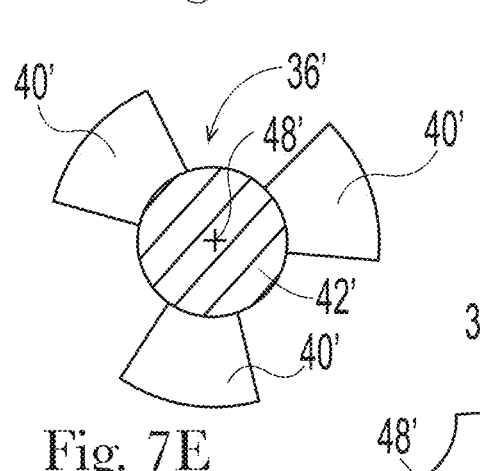
Figure 7F:
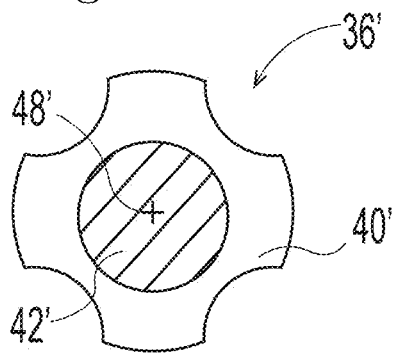
Figure 7G:
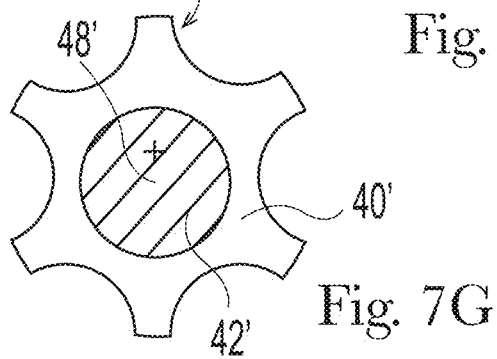

FIGS. 7A-7G are top view schematic illustrations of examples of different configurations of the second plurality of projections 36'. In such examples, the second distal portions 40' may not be the same shape as the shape of the second distal ends 42' (see e.g., FIGS. 7B-7G). In another example, the second distal portion 40' may be the same or a similar shape as the shape of the second distal ends (see e.g., FIG. 7A). Referring to FIGS. 7C-7E, the second distal portions 40' may not fully surround the second central longitudinal axes 48' of the second plurality of projections 36'. In such an instance, a compressed region or densified area in the formed substrate 2 may not fully surround a three-dimensional element. Referring to FIGS. 7E and 7G, the second distal portions 40' may fully surround the second central longitudinal axes 48' of the second plurality of projections 36'. In such an instance, a compressed region or densified area in the formed substrate 2 may fully surround a three-dimensional element.

FIGS. 8A-8F are top view schematic illustrations of examples of different configurations of the first plurality of projections 20'. The side walls 28' may fully surround the first central longitudinal axis 32' (see e.g., FIGS. 8C, 8E and 8F). In other instances, the side walls 28' may not fully surround the first central longitudinal axis 32' (see e.g., FIGS. 8A, 8B, and 8D). In some examples, the configuration of the side walls of the first plurality of projections 20 may or may not match the configuration of the second distal portions of the second plurality of projections.

In some instances, the first plurality of projections, from a top view, may have a machine directional length that is shorter than a cross-directional width due to the speed at which the substrate is produced to prevent, or at least inhibit distortion in the formed apertures. Stated another way, the machine directional length may be shorter than the cross-directional width such that round apertures are formed. If the machine directional length of the first plurality of projections is the same as the cross-directional width, ovate (elongated in MD) apertures may be formed owing to the speed at which the substrate is produced. The second plurality of projections may be designed in a similar fashion for the same reason.

Figure 9:
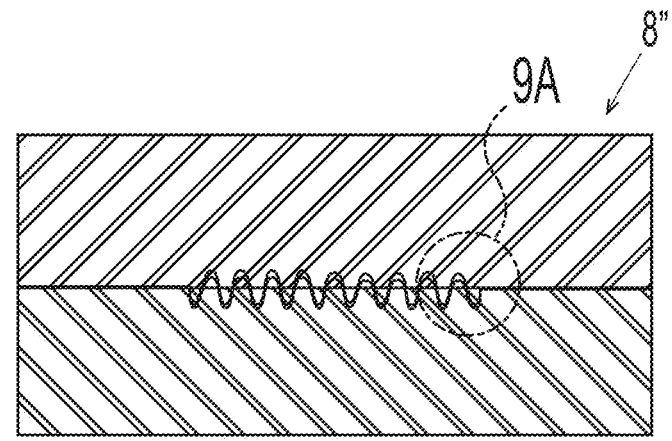
FIG. 9 is a cross-sectional view of a portion of a first roll and a portion of a second roll intermeshed with each other.
Figure 9A:
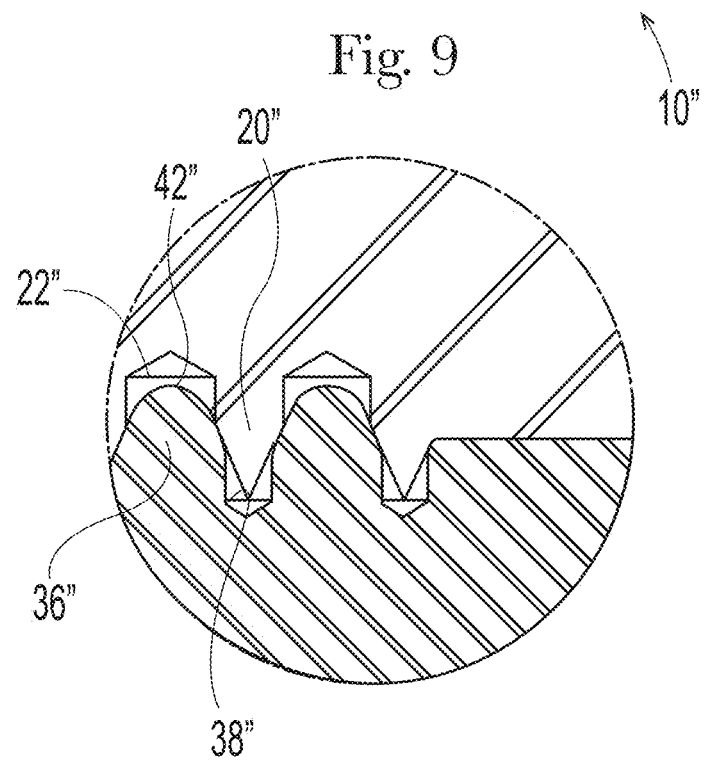
FIG. 9A is a cross-sectional blown up view of detail 9A of FIG. 9.

FIG. 9 is a cross-sectional view of a portion of a first roll 8 and a portion of a second roll 10 intermeshed with each other. FIG. 9A is a cross-sectional blown up view of detail 9A of FIG. 18. FIGS. 9 and 9A illustrate other forms of the portions of the first and second rolls 8, 10. In FIGS. 9 and 9A, the same reference numbers reflect the same components as discussed with respect to FIGS. 2-4. The second distal ends 42" of the second plurality of projections 36" have an arcuate or dome-like shape instead of a flat distal end 42 as illustrated in other figures.

The precursor substrate 4 may be heated before the nip 6, in the nip 6, and/or after the nip 6. The precursor substrate 4 or the formed substrate 2 may be heated by blowing hot air through the precursor substrate 4 or formed substrate 2 (i.e., "air-through), by running the entire precursor substrate 4 or formed substrate 2 through a heat tunnel, by running a surface of the precursor substrate 4 or substrate 2 over a heated roll (to only heat the surface) or a nip between two heated rolls (to heat both surfaces), by radiation, and/or by heating the first and/or second rolls 8, 10, for example. Hot air may also be blown through conduits in one or more of the rolls 8, 10, to heat the precursor substrate 4. Heating the precursor substrate 4 before the precursor substrate 4 enters the nip may cause the precursor substrate 4 to absorb enough heat to allow the precursor substrate 4 or polymers in the precursor substrate 4 to flow under pressure and create bonds or welds to stabilize the apertures 56 and/or three-dimensional elements 54. Heating the formed substrate 2 after the nip may cause the three-dimensional elements 54 and the apertures 56 to be "set" into the substrate. In some cases, it may be desirable to input energy into the precursor substrate or substrate to either aid in the formation of the three-dimensional elements 54 and apertures 56 and/or to help "set" the three-dimensional elements and/or apertures. This input energy may also help to stabilize the substrate and may promote better fiber fusion in the substrate. Providing input energy to the substrate may also provide the three-dimensional elements of the substrate, or the substrate as a whole the ability to better resist compression due to packaging.

If the precursor substrate 4 is heated upstream of the nip, it may be cooled in the nip or downstream from the nip. Cooling may be accomplished by maintaining the first and second rolls 8, 10 at ambient temperature, by running the formed substrate 2 over a cooled roll, or by cooling the first and second rolls 8, 10. The first and second rolls 8, 10 may be at a temperature cooler than a temperature of the precursor substrate. Cooling may also be accomplished in the nip by blowing ambient or cooled air into the nip. Cooling may also be accomplished by ambient air or by blowing ambient air onto the substrate downstream of the nip or by providing a cooling source, such as cooled air blowing on the substrate or by cooled rolls. Cooling may also be accomplished through cooling in the nip (cooled first and second rolls 8, 10) and downstream of the nip (cooled rolls, blowing ambient air, or blowing cooled air).

If the precursor substrate 4 is heated in the nip, it may be cooled downstream of the nip. Cooling may be accomplished downstream of the nip by ambient air, by blowing ambient air, or by providing a source of cooling, such as blown cooled air or cooled rolls.

Figure 10:
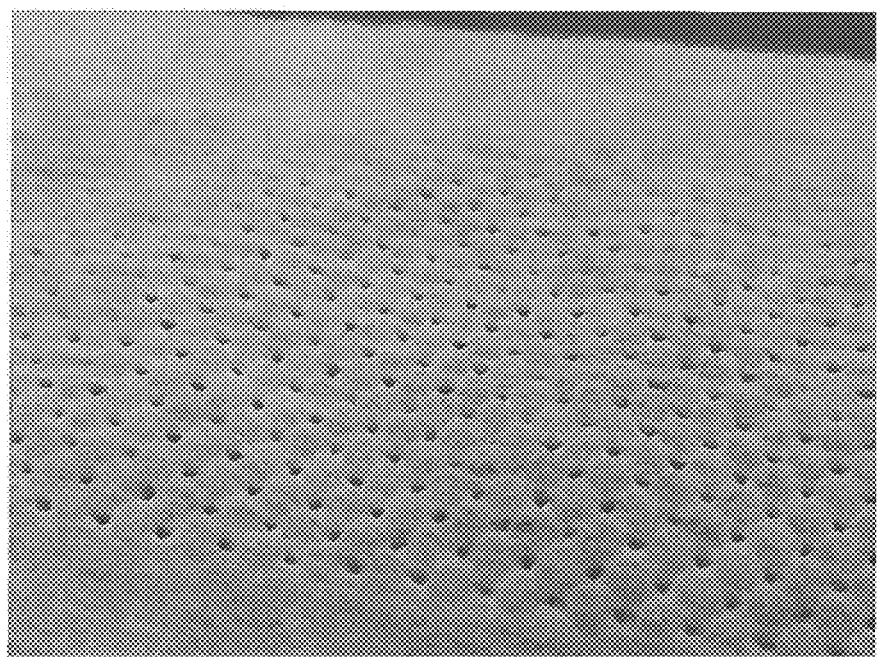
FIG. 10 is a top perspective view of an example three-dimensional apertured substrate produced by the first and second rolls 8, 10 of FIG. 1.
Figure 11:
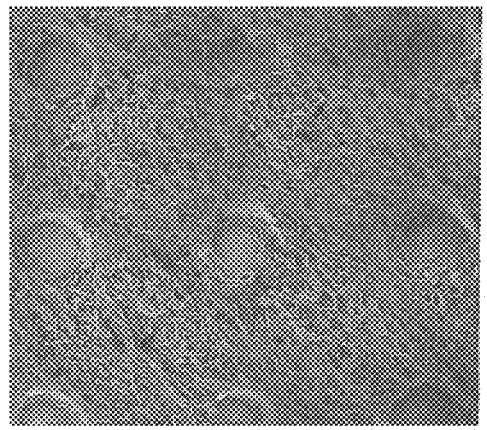
FIG. 11 is a top view of an example three-dimensional, apertured substrate produced by the first and second rolls 8, 10 of FIG. 1.
Figure 12:
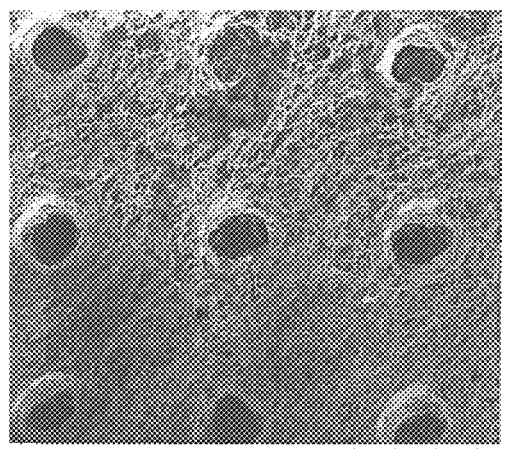
FIG. 12 is a back view of the example three-dimensional, apertured substrate of FIG. 11.
Figure 13:
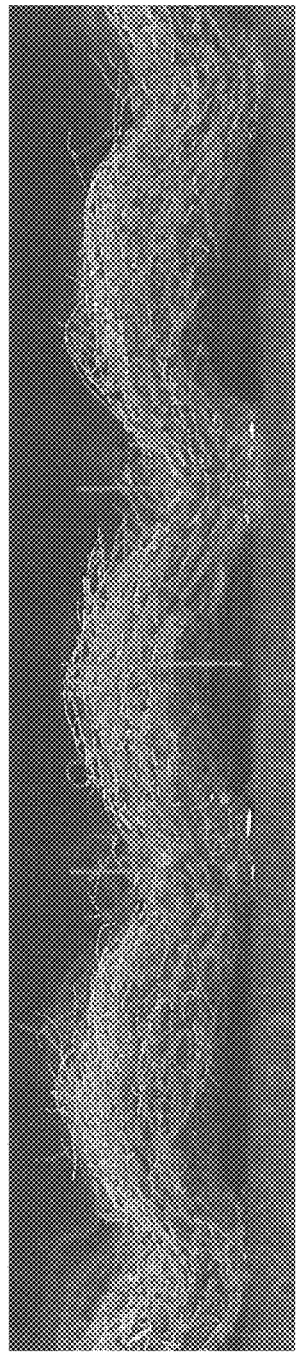
FIG. 13 is a cross-sectional view taken through the example three-dimensional, apertured substrate of FIG. 11.
Figure 23:
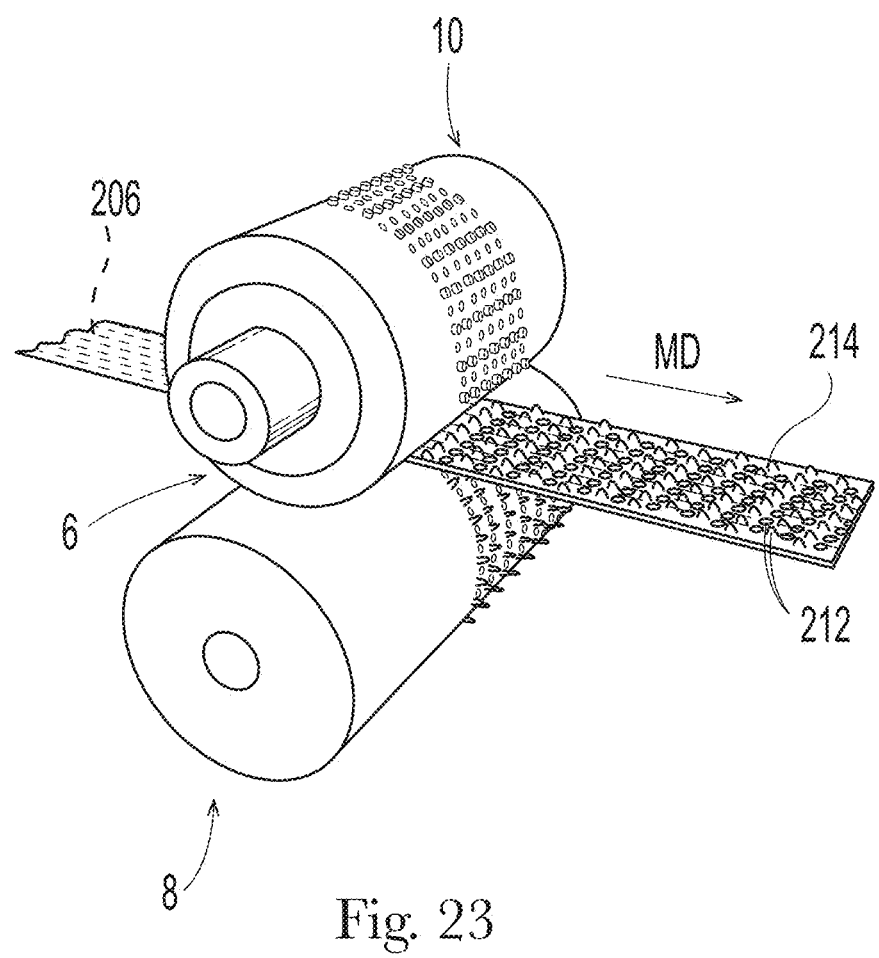
FIG. 23 is a perspective view of an elastic belt being conveyed through a nip between a first roll and second roll to create apertures and three-dimensional elements in the elastic belt.

FIG. 10 is a top perspective view of an example three-dimensional, apertured substrate produced by the first and second rolls 8, 10 of the present disclosure. FIG. 11 is a top view of an example three-dimensional, apertured substrate produced by the first and second rolls 8, 10 of the present disclosure. FIG. 12 is a back view of the example three-dimensional, apertured substrate of FIG. 11. FIG. 23 is a cross-sectional view taken through the example three-dimensional, apertured substrate of FIG. 11.

Figure 14:
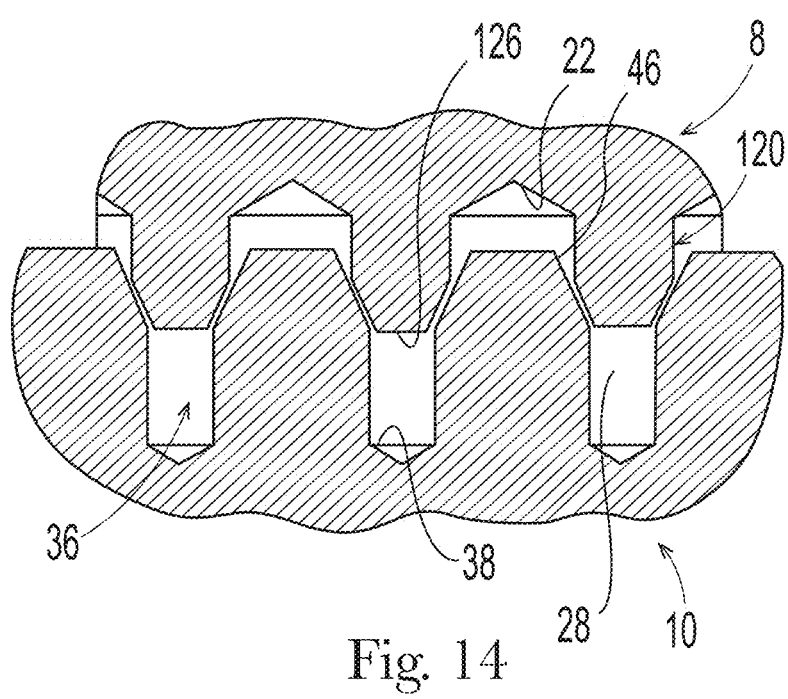
FIG. 14 is a simplified schematic cross-sectional example illustration of the rolls 8, 10 that are configured primarily for creating three-dimensional elements and compressed regions in the precursor substrate 4 and not apertures.
Figure 16:
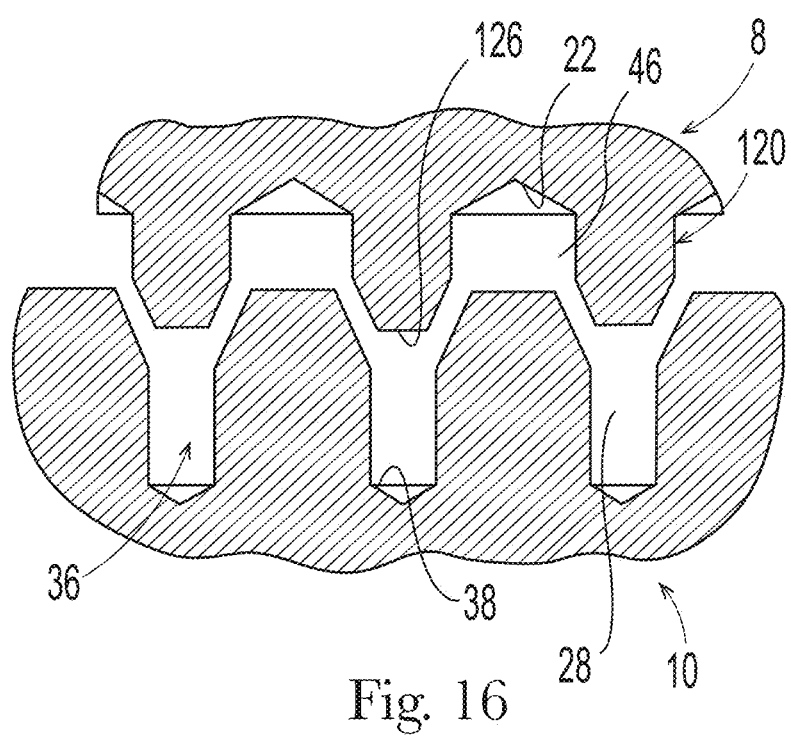
FIG. 16 is a simplified schematic cross-sectional example illustration of the rolls 8, 10 that are configured primarily for creating three-dimensional elements and compressed regions in the precursor substrate 4 and not apertures.

FIG. 14 illustrates a simplified schematic cross-sectional example illustration of the rolls 8, 10 that are configured primarily for creating three-dimensional elements and compressed regions in the precursor substrate 4 and not apertures. In FIG. 14, distal ends 126 of the first plurality of projections 120 may form flat or rounded surfaces so as to not aperture the precursor substrate. The second plurality of projections 36 and the second roll 10 generally may remain the same as described above. FIG. 16 illustrates a simplified schematic cross-sectional example illustration of the rolls 8, 10 of FIG. 14 with less engagement with each other. This level of engagement may be used for thicker substrates, for example, or when less compression is desired.

Figure 15:
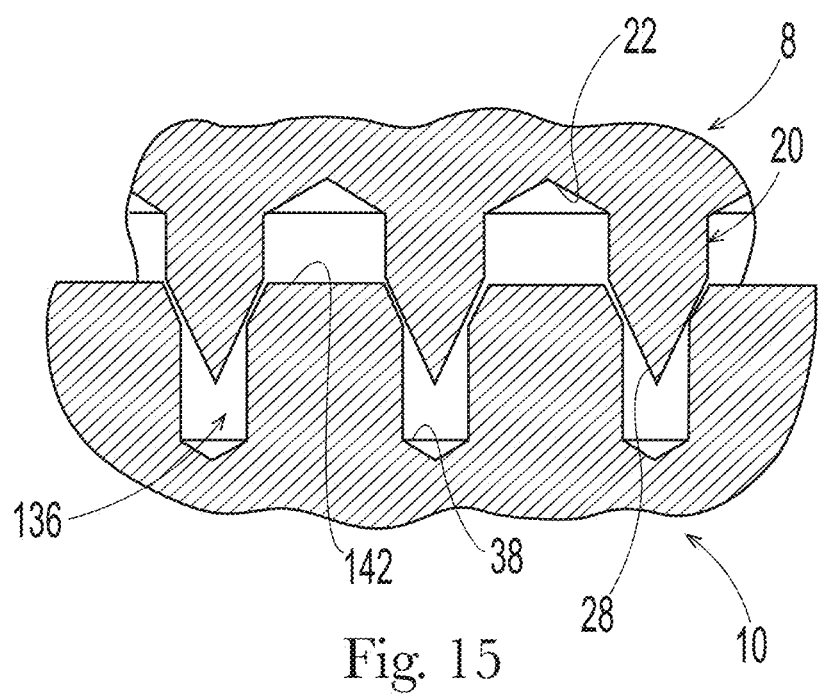
FIG. 15 is a simplified schematic cross-sectional example illustration of the rolls 8, 10 that are configured primarily for creating apertures and compressed regions in the precursor substrate 4 and not three-dimensional elements or more limited (e.g., less height) three dimensional elements compared to the rolls 8, 10 of FIG. 4.
Figure 17:
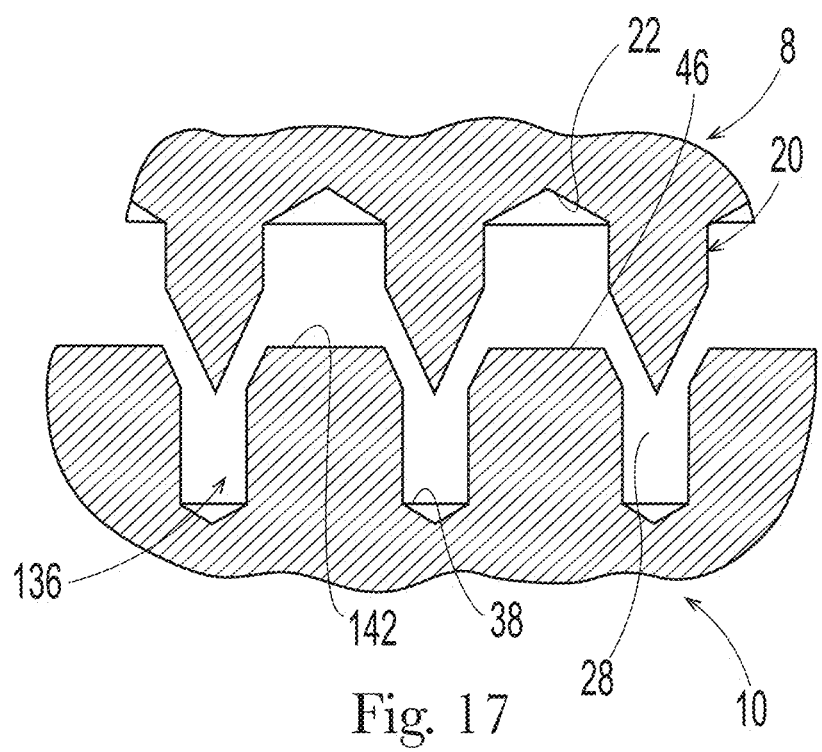
FIG. 17 is a simplified schematic cross-sectional example illustration of the rolls 8, 10 that are configured primarily for creating apertures and compressed regions in the precursor substrate 4 and not three-dimensional elements or more limited (e.g., less height) three dimensional elements compared to the rolls 8, 10 of FIG. 4 and FIG. 15.

FIG. 15 illustrates a simplified schematic cross-sectional example illustration of the rolls 8, 10 that are configured primarily for creating apertures and compressed regions in the precursor substrate 4 and not three-dimensional elements or more limited (e.g., less height) three dimensional elements compared to the rolls 8, 10 of FIG. 4. In FIG. 15, second distal ends 142 of the second plurality of projections 136 may form flat or rounded surfaces, for example to eliminate three-dimensional element formation or to reduce the height of the three-dimensional elements in the precursor substrate. The first plurality of projections 20 and the first roll 8 generally may remain the same as described above. FIG. 17 illustrates a simplified schematic cross-sectional example illustration of the rolls 8, 10 of FIG. 15 with less engagement with each other. This level of engagement may be used for thicker substrates, for example, or when less compression and/or smaller apertures are desired.

Figure 18:
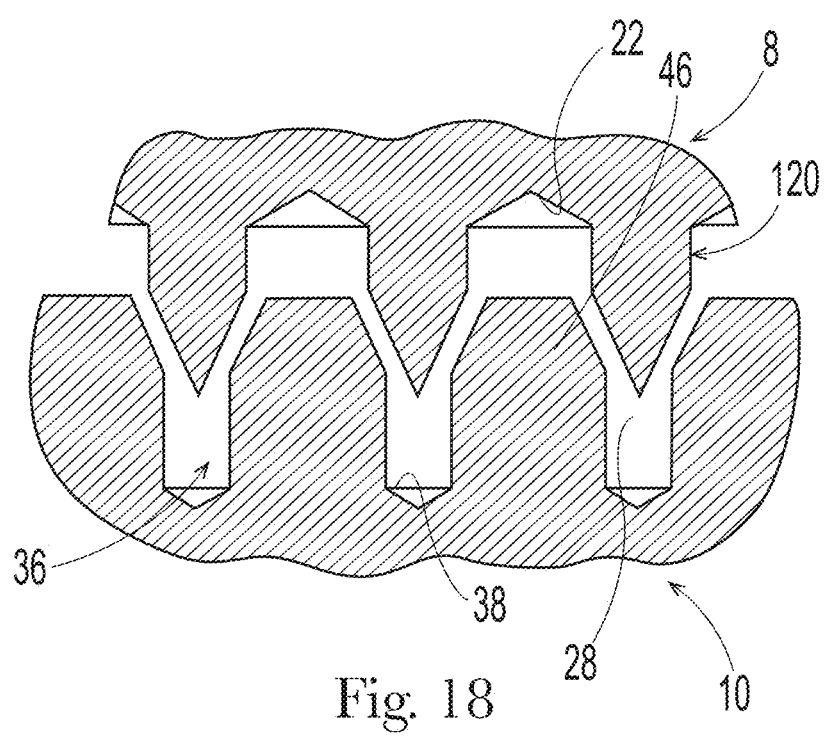
FIG. 18 is a simplified schematic cross-sectional example illustration of the rolls 8, 10 that are configured for creating apertures and three-dimensional elements in the precursor substrate 4, but not compressed regions.

FIG. 18 illustrates a simplified schematic cross-sectional example illustration of the rolls 8, 10, like FIG. 4, but with more separation between the rolls 8, 10. In such an instance, the rolls 8, 10 may be set apart from each other such that only apertures and three-dimensional elements are formed in the precursor substrate, without compressed regions being formed between the side walls 28 and the shoulders 46. In some instances, portions of the precursor substrate 4 may be slightly compressed between the side walls 28 and the shoulders 46, but not to the extent of compression that would result from the rolls 8, 10 of FIG. 4. As such, the center-to-center distance of the first central longitudinal axis 32 of the first roll may be adjusted with respect to the second central longitudinal axis 32 of the second roll to determine the amount of compression in portions of the precursor substrate 4 between the side walls 28 and the shoulders 46. In some instances, more compression may be desired and, in other instances, less compression may be desired. The thickness of the precursor substrate 4 may also be a factor to consider in setting the center-to-center distance of the rolls 8, 10. This concept of setting the center-to-center distance of the rolls may also apply to any of the other example roll configurations set forth herein.

Figure 19:
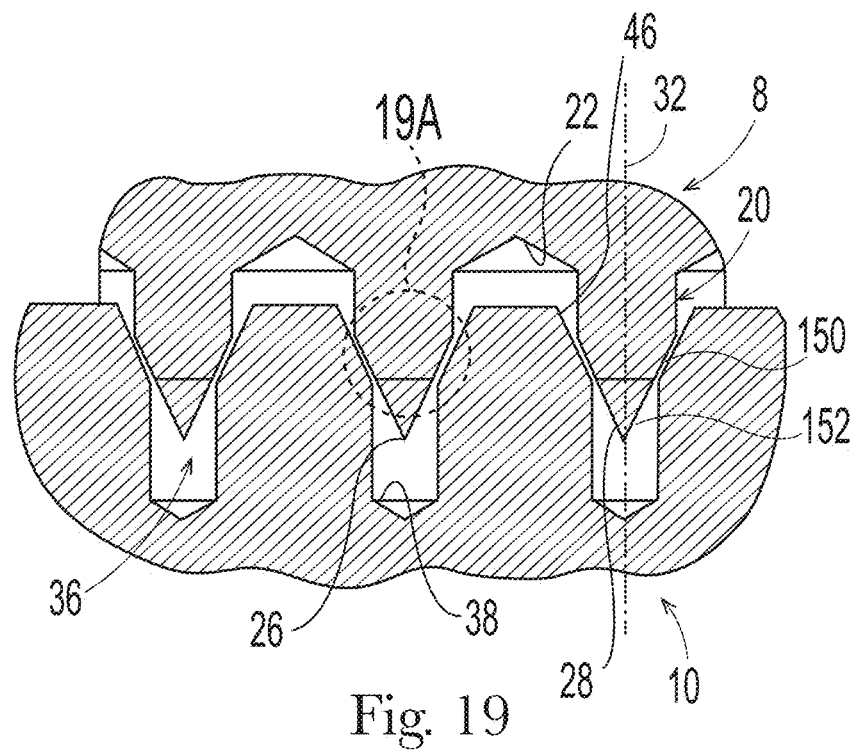
FIG. 19 is a simplified schematic cross-sectional illustration of a portion of a first roll of intermeshed with a portion of a second roll.
Figure 19A:
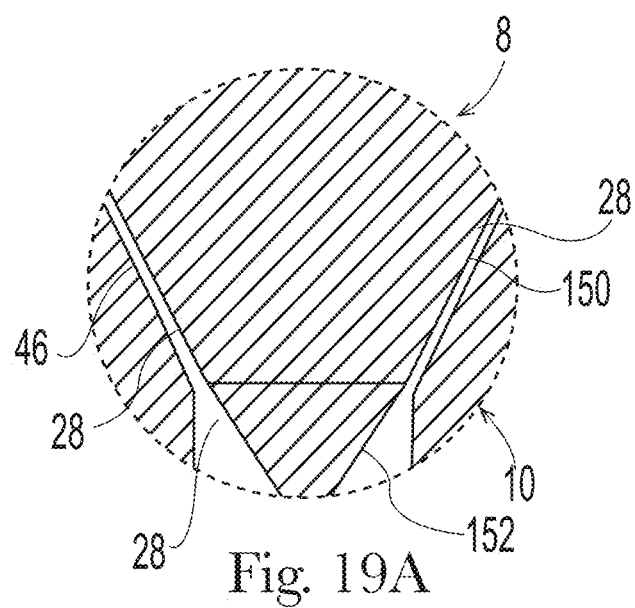
FIG. 19A is an exploded view of region 19A in FIG. 19.

FIG. 19 illustrates a simplified schematic cross-sectional example illustration of a portion of a first roll 8 intermeshed with a portion of a second roll 10. FIG. 19A is an exploded view of region 19A in FIG. 19. The second roll 10 may be substantially the same as, or the same as, the second roll 10 of FIG. 17 or 18. At least some of, or all of, the projections 20 may comprise first distal portions 24 comprising elongated aperturing structures comprising side walls 28. The side walls 28 may have a first portion 150 having a first angle and a second portion 152 having a second angle. The angles are measured relative to a central longitudinal axis 32 of a projection 20. The second portion 152 may be more proximal to the first distal end 26 or point than the first portion 150. The first angle may be lower than or steeper than the second angle. The first angle of the first portion 150 may be in the range of about 20 degrees to about 50 degrees, about 25 degrees to about 40 degrees, about 30 degrees to about 40 degrees, about 35 degrees, about 36 degrees, or about 37 degrees, specifically reciting all 0.1 degree increments within the specified ranges and all ranges formed therein or thereby. The second angle of the second portion 152 may be in the range of about 30 degrees to about 60 degrees, about 35 degrees to about 55 degrees, about 40 degrees to about 50 degrees, about 46 degrees, about 47 degrees, or about 48 degrees, specifically reciting all 0.1 degree increments within the specified ranges and all ranges formed therein or thereby. By having a smaller angle or steeper sidewall in the first portion 150 and a larger angle and less steep sidewall in the second portion 152, the overall longitudinal length of the projections 20 may be shorter compared to a projection having a first distal portion with only one angle. Shorter projections allow for easier engagement between the first and second rolls 8, 10. Any of the example rolls configured for aperturing may have the features of the first plurality of projections 20 described in this paragraph in reference to FIGS. 19 and 19A. Further, the features of the first plurality of projections 20 may be used when merely making apertures and not there-dimensional projections (e.g., FIGS. 15 and 17).

The shoulders 46 may taper inwards toward the point of the first plurality of projections 20 or may have the same angle as the first portion 150.

The various rolls may be formed by materials that have good thermal conductivity and that are easy to machine. Example materials include cooper, aluminum, and brass, for example. In some instances, the rolls may be steel or hardened steel. The rolls may have various surface coatings to reduce wear.

Figure 20:
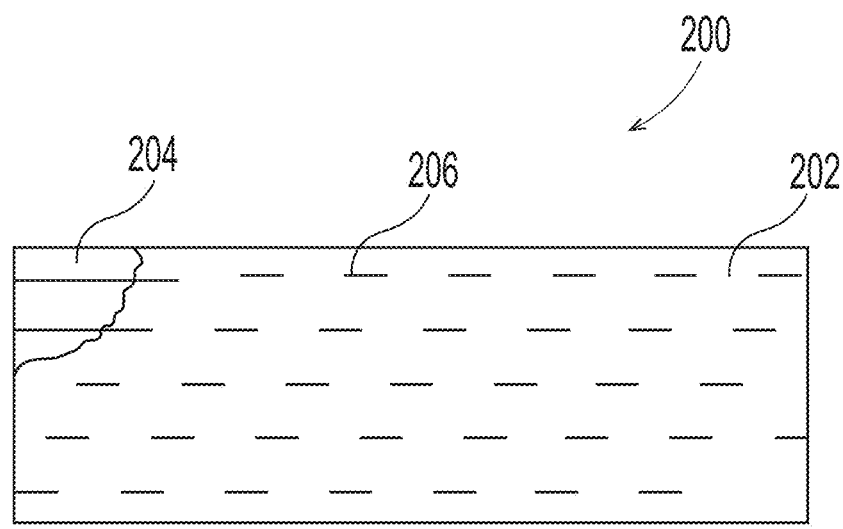
FIG. 20 is a top view of an elastic belt without apertures or three-dimensional elements.

Referring to FIG. 20, an example elastic belt 200 is illustrated. The elastic belt 200 is shown before being processed through the various first and second rolls 8 and 10 described herein. The elastic belt 200 may comprise a first nonwoven substrate 202, a second nonwoven substrate 204, and a plurality of elastic strands 206 disposed intermediate the first nonwoven substrate 202 and the second nonwoven substrate 204. The elastic strands 206 may have any suitable spacing between them depending on the desired application of the elastic belt. More than two nonwoven substrates may be provided in an elastic belt for softness, aesthetics, and/or other purposes. The elastic belts of the present disclosure may be free of films.

Figure 21:
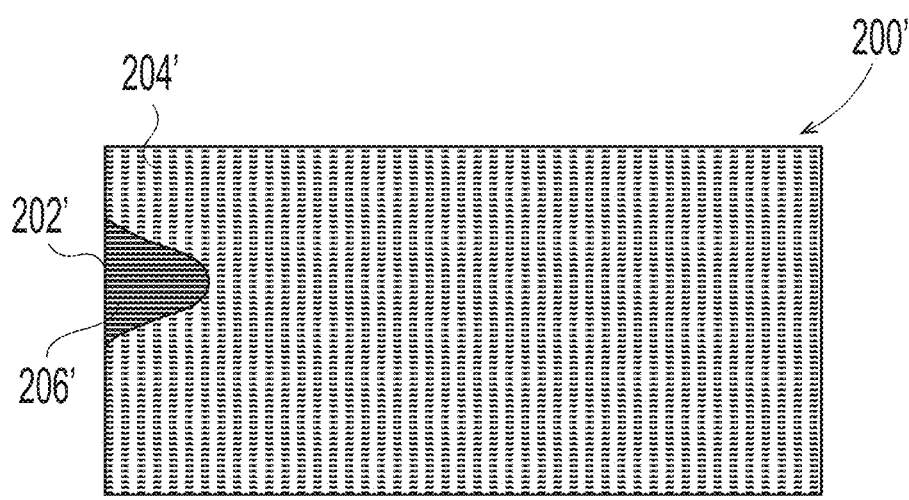
FIG. 21 is a top view of another elastic belt without apertures or three-dimensional elements.

Referring to FIG. 21, another example elastic belt 200' is illustrated. The elastic belt 200' is shown before being processed through the various first and second rolls 8 and 10 described herein. The elastic belt 200' may comprise a first nonwoven substrate 202', a second nonwoven substrate 204', and a plurality of elastic strands 206' disposed intermediate the first nonwoven substrate 202' and the second nonwoven substrate 204'. The elastic strands 206' may have any suitable spacing between them depending on the desired application of the elastic belt. It is notable that the elastic strands 206' of the elastic belt 200' are much finer and closer together than the elastic strands 206 of the elastic belt 200. Such elastic strands are discussed in further detail in U.S. Provisional Patent Application No. 62/553,538, filed on Sep. 1, 2017, titled "ELASTOMERIC LAMINATE(S) CONFIGURED TO PERFORM IN VARIOUS COMPONENTS OF A DISPOSABLE ABSORBENT ARTICLE." The process of manufacturing such laminates is disclosed in U.S. Provisional Patent Application Nos. 62/436,589, filed on Dec. 20, 2016, titled "METHODS AND APPARATUSES FOR MAKING ELASTOMERIC LAMINATES WITH ELASTIC STRANDS UNWOUND FROM BEAMS," 62/483, 965, filed on Apr. 11, 2017, titled "METHODS AND APPARATUSES FOR MAKING ELASTOMERIC LAMINATES WITH ELASTIC STRANDS PROVIDED WITH A SPIN FINISH," 62/553,149, filed on Sep. 1, 2017, titled "METHODS AND APPARATUSES FOR MAKING ELASTOMERIC LAMINATES WITH ELASTIC STRANDS PROVIDED WITH A SPIN FINISH," 62/553,171, filed on Sep. 1, 2017, titled "METHODS AND APPARATUSES FOR MAKING ELASTOMERIC LAMINATES WITH ELASTIC STRANDS," 62/581,278, filed on Nov. 3, 2017, titled "APPARATUSES AND METHODS FOR MAKING ABSORBENT ARTICLES WITH ELASTOMERIC LAMINATES,". More than two nonwoven substrates may be provided in an elastic belt for softness, aesthetics, and/or other purposes.

Figure 22:
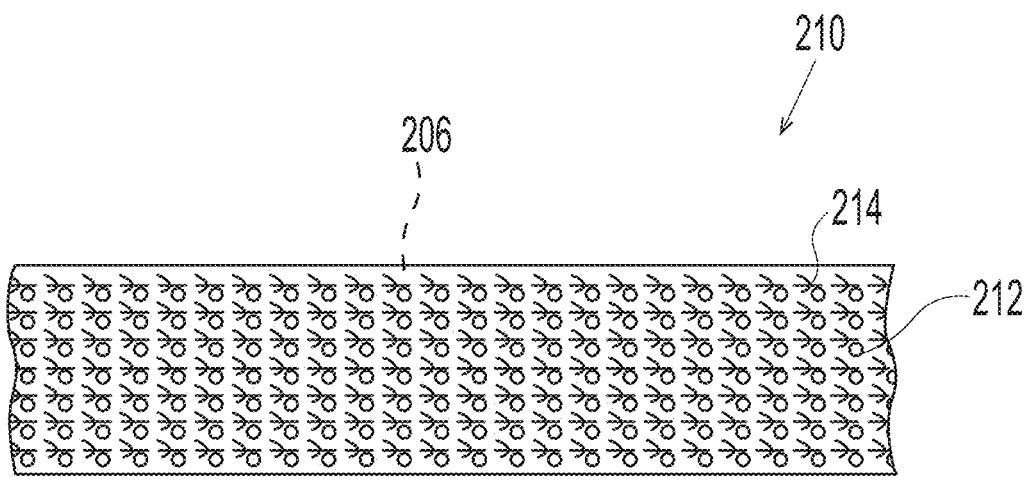
FIG. 22 is a top view of an elastic belt with apertures and three-dimensional elements.

FIG. 22 is a top view of an example elastic belt 210 after being conveyed through the nip 6 between the first roll 8 and the second roll 10. The elastic belt 210 has apertures 212 and three-dimensional elements 214, although an elastic belt may only have three-dimensional elements 214 or may only have apertures 212 depending on the versions of the first and second rolls 8, 10 used. When creating apertures, the points of the first distal ends 26 of the first roll 8 may push the elastic strands 206 and/or 206' aside such that the elastic strands are not broken.

In some instances, the elastic strands of the present disclosure may comprise multi-filament elastic strands, such as 3 to 20 filaments forming a single elastic strand, for example. The advantages of using multiple-filament elastic strands are discussed below.

FIG. 23 is a perspective view of the elastic belt being conveyed in a machine direction "MD" through a nip 6 formed between the first roll 8 and the second roll 10 to be formed into the elastic belt 210 illustrated in FIG. 22 having apertures 212 and/or three-dimensional elements 214. The first roll 8 may be the same as described herein and the second roll 10 may be the same as described herein.

Figure 24:
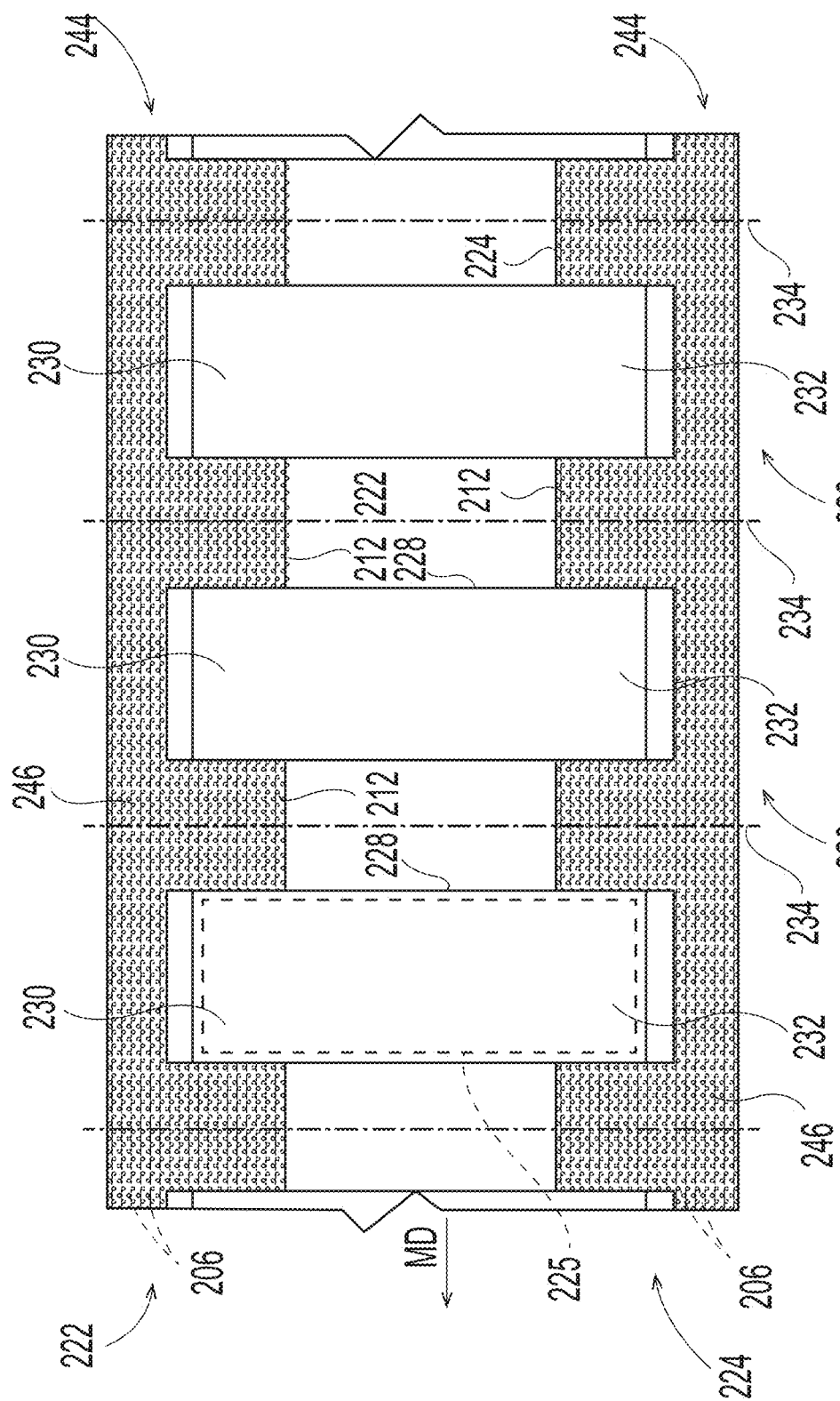
FIG. 24 is a top view of a web of absorbent articles comprising two elastic belts with apertures and/or three-dimensional elements.

FIG. 24 is a top view of an uncut web of absorbent articles 220. The web of absorbent articles 220 comprises a first elastic belt 222 and second elastic belt 224. Each of the elastic belts 222, 224 may have a plurality of elastic strands 206 (or 206') extending in the machine direction "MD". A plurality of chasses 228 of absorbent articles are attached to the elastic belts 222, 224 on their end portions 230, 232. The absorbent article chasses 228 may each comprise a topsheet 221, a backsheet 223, and an absorbent core 225 disposed at least partially intermediate the topsheet and the backsheet. Areas of overlap between the chasses 228 and the elastic belts 222, 224 may be formed where the end portions 230, 232 of the chasses 228 are overlapped with the elastic belts 222, 224. The web of absorbent articles 220 may be separated along cut lines 234 and then formed into pants, for example. The first and second elastic belts 222, 224 may define apertures 212 formed therein. In other instances, the first and second elastic belts 222 and 224 may comprise three-dimensional elements. In still other instances, the first and second elastic belts 222 and 224 may comprise apertures and three-dimensional elements.

Figure 25:
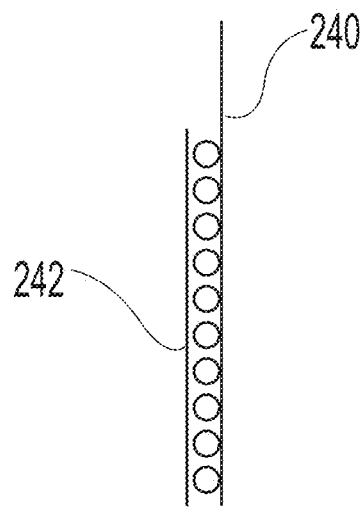
FIG. 25 is a cross-sectional example illustration of an elastic belt where two nonwoven substrates have different widths.
Figure 26:
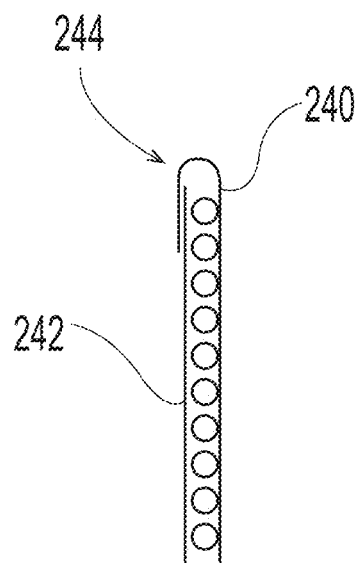
FIG. 26 is a cross-sectional example illustration of the elastic belt of FIG. 25 with a portion of one nonwoven substrate folded over the other nonwoven substrate.

Referring to FIGS. 24, 25, and 26, the first and second elastic belts 222 and 224 may comprise a first nonwoven substrate 240 and a second nonwoven substrate 242. The first nonwoven substrate 240 may have a first cross-directional width (in reference to FIG. 24 and arrow MD) and the second nonwoven substrate 242 may have a second cross-directional width. The first cross-directional width may be larger than the second cross-directional width. Having a first nonwoven substrate 240 with a larger cross-directional length allows a portion 244 of the first nonwoven substrate 240 to be folded over a portion of the second nonwoven substrate 242 to create a smooth waist edge in the elastic belt and eliminate rough waist edges. The portion 244 of the first nonwoven substrate folded over the second nonwoven substrate may create a fold over region 246 in the elastic belts 222 and 224. FIG. 25 illustrates a cross-sectional example illustration of the elastic belts 222, 224 before fold over and FIG. 26 illustrates a cross-sectional example illustration of the elastic belts 222, 224 after fold over.

It is desirable to fold over the fold over regions 246 prior to conveying the web of absorbent articles through nip 6 between the first and second rolls 8, 10. In this fashion, apertures and/or three-dimensional elements may be formed through/in the elastic belts 222, 224, including in the fold over regions 246.

Figure 27:
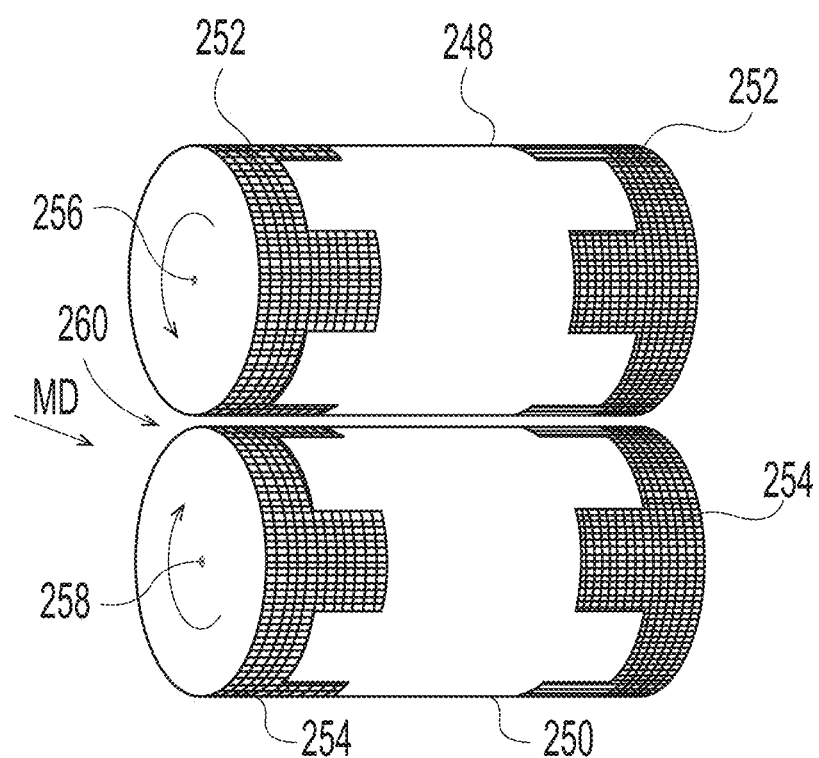
FIG. 27 is a perspective view of a first roll and a second roll having a pattern suitable for aperturing and/or creating three-dimensional elements in a web of absorbent articles, such as the web of absorbent articles illustrated in FIG. 24.

While it is desirable to create at least apertures in some of the fold over regions 246 of the elastic belts 222, 224 to increase breathability, it is not desirable to create apertures through the chasses 228, or the absorbent cores 225 of the chasses 228, as the apertures could cause leakage of bodily exudates. Apertures through the chassis 228, such as the absorbent cores 225, could cause apertures through a backsheet film of the chassis 228, thereby potentially leading to bodily exudate leakage. An example pair of rolls that could accomplish the desired aperturing are illustrated in FIG. 27. The pair of rolls has a first roll 248 and a second roll 250. First shaded portions 252 of the first roll 248 may have the same features as first roll 8 herein, and the second shaded portions 254 of the second roll 250 may have the same or similar features as the second roll 10 herein. As such, apertures (and/or three-dimensional elements) may only be created in the fold over regions 246 in areas not including a chassis 228. As a result, apertures (and/or three-dimensional elements) may not be created in the chassis 228.

Referring again to FIG. 27, the first roll 248 may have a first rotational axis 256 and the second roll 250 may have a second rotational axis 258. The first roll 248 may rotate about the first rotational axis 252 in the direction indicated by the arrow. Likewise, the second roll 250 may rotate about the second rotational axis 254 in the direction indicated by the arrow. The second roll 250 may be rotated in an opposite direction as the first roll 248. The first rotational axis 256 may be positioned generally parallel to or parallel to the second rotational axis 258 such that a nip 260 may be formed intermediate the first roll 248 and the second roll 250.

FIG. 24A is a top view of two elastic belts 222' and 224' being conveyed in a machine direction (MD). Each of the first and second elastic belts 222' and 224' may have a plurality of elastic strands 206 (or 206') extending in the machine direction "MD". The first and second elastic belts 222', 224' may define apertures 212 formed therein. In other instances, the first and second elastic belts 222' and 224' may comprise three-dimensional elements. In still other instances, the first and second elastic belts 222' and 224' may comprise apertures and three-dimensional elements.

The elastic belts 222' and 224' may have a folded over portion 244' similar to that described with respect to FIGS. 25 and 26 above. The folded over portion 244' of the elastic belts 222' and 224' may be smaller in the cross-direction than the folded over portion 244 described above. In other instances, the elastic belts may not comprise any folded over portion. The folded over portion 244' may create a folded over region 246' in the first and second elastic belts 222' and 224'.

Figure 27A:
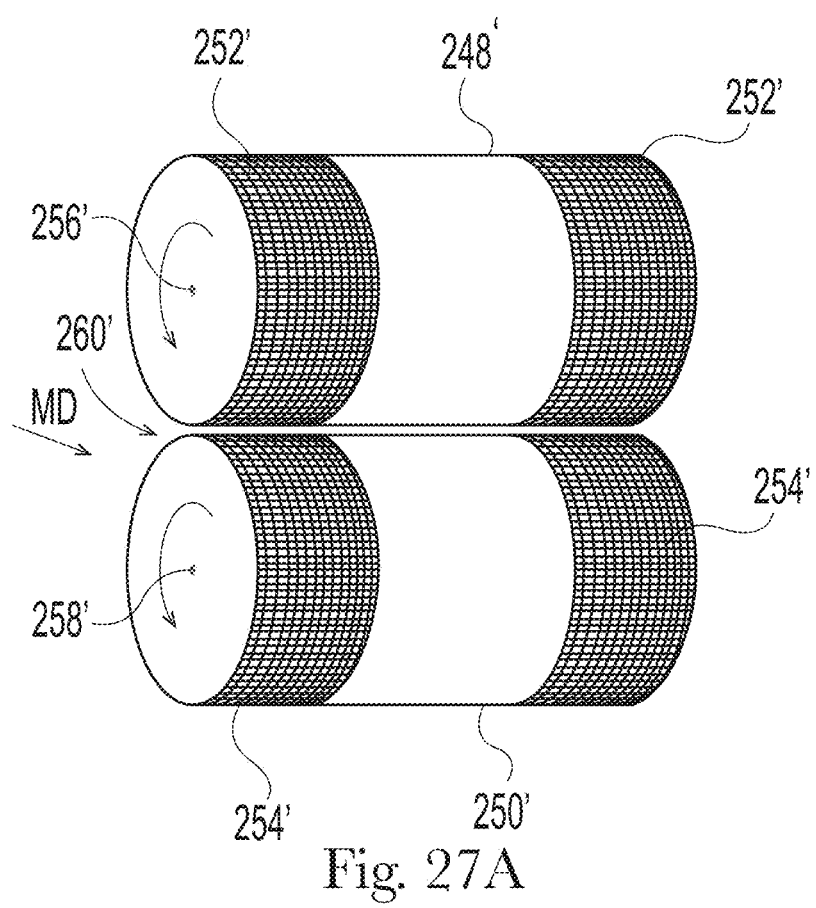
FIG. 27A is a perspective view of a first roll and a second roll having a pattern suitable for aperturing and/or creating three-dimensional elements in the elastic belts for absorbent articles illustrated in FIG. 24A.

To create the elastic belts 222' and 224', first and second rolls 248' and 250' of FIG. 27A may be used. The first roll 248' may have a first rotational axis 256' and the second roll 250' may have a second rotational axis 258'. The first roll 248' may rotate about the first rotational axis 252' in the direction indicated by the arrow. Likewise, the second roll 250' may rotate about the second rotational axis 254' in the direction indicated by the arrow. The second roll 250' may be rotated in an opposite direction as the first roll 248'. The first rotational axis 256' may be positioned generally parallel to, or parallel to, the second rotational axis 258' such that a nip 260' may be formed intermediate the first roll 248' and the second roll 250'.

In the forms illustrated in FIGS. 24A and 27A, apertures 212 and/or three-dimensional elements may be formed in the elastic belts 222' and 224' prior to a plurality of chasses being attached to the elastic belts (as shown in FIG. 24). In such an instance, the first and second rolls 248' and 250' may be used. The elastic belts 222' and 224' may or may not have the folded over region 246'. In such an instance, the first and second rolls 248' and 250' do not need to be pitched (i.e., absorbent article size specific) and no precautions have be to taken to avoid aperturing and/or creating three-dimensional elements in the chassis, or portions thereof, such as the backsheet or absorbent core. In some instances, only one elastic belt, or portions thereof, may be apertured and/or have three-dimensional elements created therein.

Regarding the first and second rolls 248' and 250', first shaded portions 252' of the first roll 248' may have the same or similar features as first roll 8 herein, and second shaded portions 254' of the second roll 250' may have the same or similar features as the second roll 10 herein. As such, apertures and/or three-dimensional elements may be created in an entire area of each belt 222' and 224'. The first and second shaded portions 252' and 254' may also be configured to create apertures and/or three-dimensional elements in less than an entire area of each belt 222' and 224'.

Instead of the first and second rolls 248 and 250, a first, separate set of rolls could be used to aperture and/or create three-dimensional elements in the first elastic belt 222 and a second, separate set of rolls could be used to aperture and/or create three-dimensional elements in the second elastic belt 224. In such a fashion, the first elastic belt 222 would be conveyed through a nip formed between the first, separate set of rolls and the second elastic belt 224 would be conveyed through a nip formed between the second, separate set of rolls. The same may apply to rolls 248' and 250'.

Figure 28:
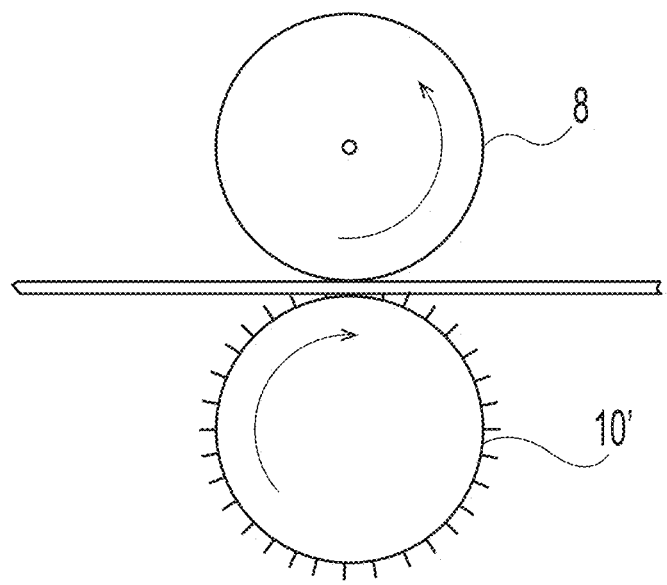
FIG. 28 is a plan view of first and second rolls used to create an apertured and/or three-dimensional element containing elastic belt, wherein the second roll comprises a brush roll.
Figure 29:
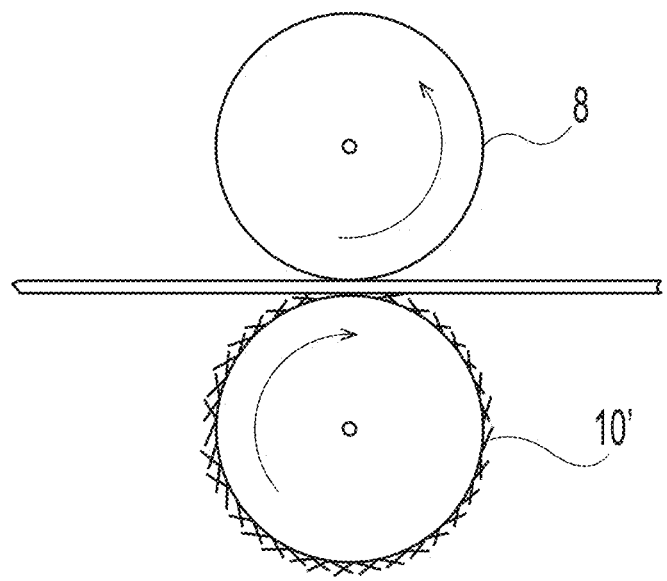
FIG. 29 is a plan view of first and second rolls used to create an apertured and/or three-dimensional element containing elastic belt, wherein the second roll comprises a felt roll.

Instead of the various second rolls illustrated herein (e.g., roll 10), the second roll could comprise a brush roll 10' (FIG. 28) or a felt roll 10" (FIG. 29). The first roll 8 could be the same as described herein and be configured to create apertures in an elastic belt. Likewise, the first roll could comprise a brush roll or a felt roll. The second roll 10' could be like the second roll 10 described herein and be configured to create three-dimensional elements in an elastic belt. The brush or felt rolls may be used like steel anvil rolls and cause the elastic belts being conveyed therethough to be pushed into the first roll or the second roll to create the apertures and/or three-dimensional elements.

Figure 30:
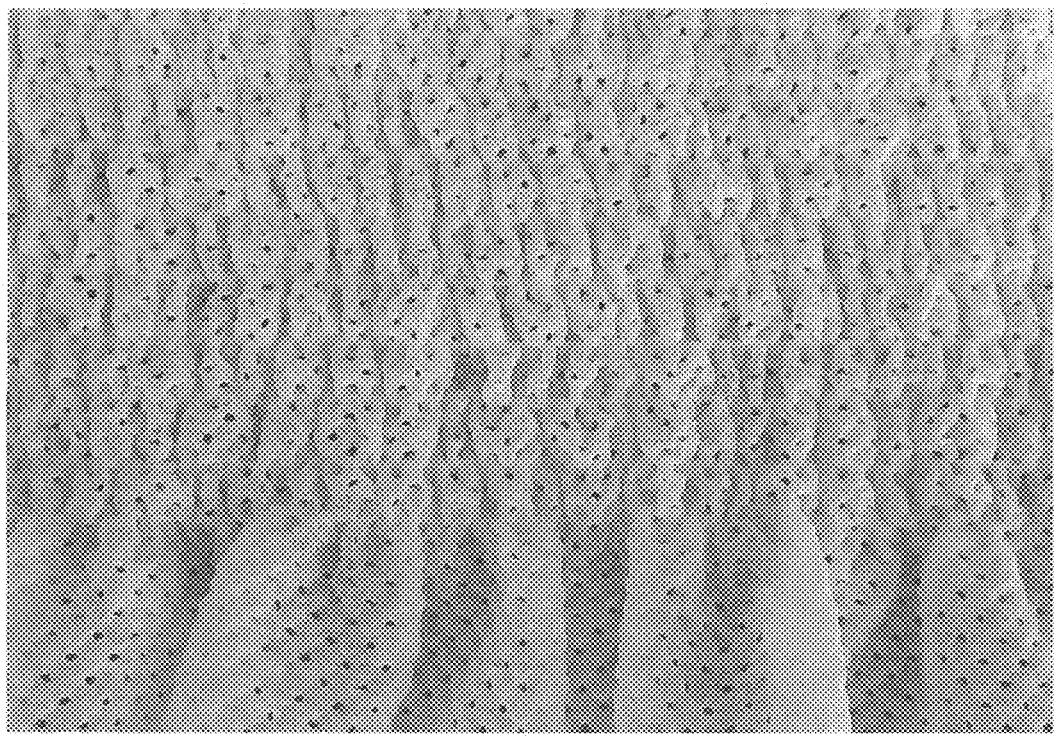
FIGS. 30-31 are photographs of portions of elastic belts with apertures and three-dimensional elements with relatively large elastic strand spacing.
Figure 31:
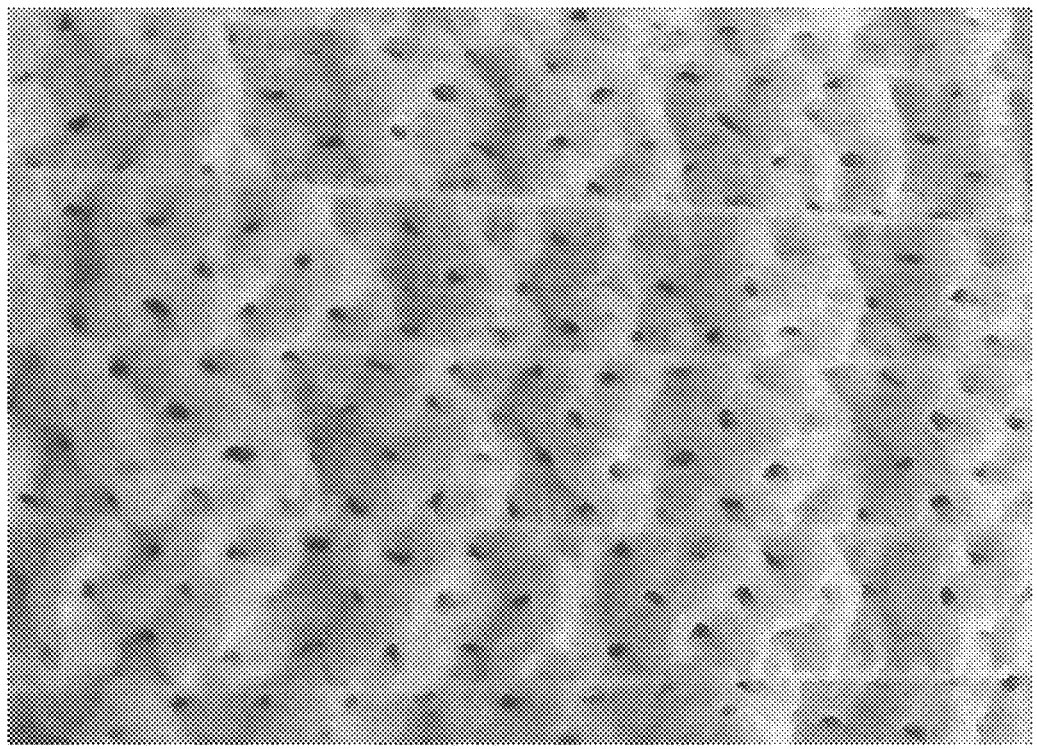
Figure 32:
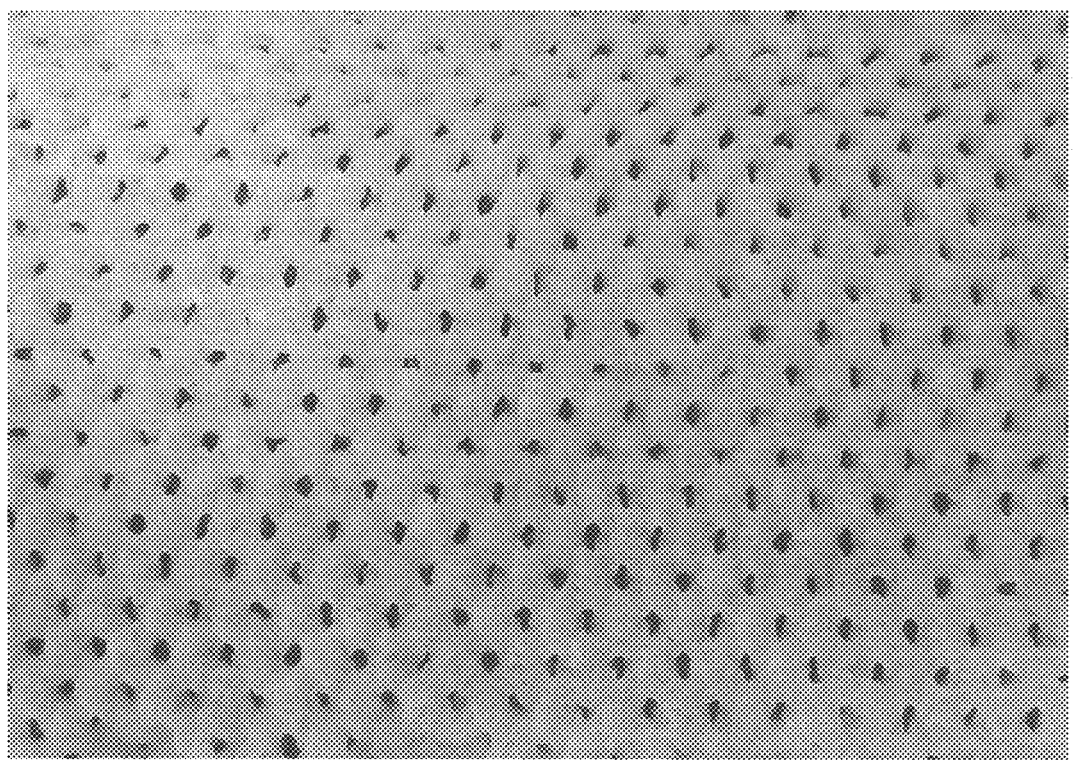
FIG. 32 is a photograph of a portion of an elastic belt with apertures and three-dimensional elements with relatively small elastic strand spacing.

FIGS. 30 and 31 are photographs of portions of elastic belts with apertures and three-dimensional elements with relatively large elastic strand spacing, such as that illustrated in FIG. 20, for example. FIG. 32 is a photograph of a portion of an elastic belt with apertures and three-dimensional elements with relatively small elastic strand spacing, such as that illustrated in FIG. 21, for example. The elastic belts of FIGS. 30-32 were processed using rolls 8 and 10, such as the rolls generally disclosed in FIGS. 2-4A and 19-19A. The elastic belts of FIGS. 30-32 and described herein are imparted a three-dimensional structure from the three-dimensional elements and from the contraction of the elastic strands.

Figure 33:
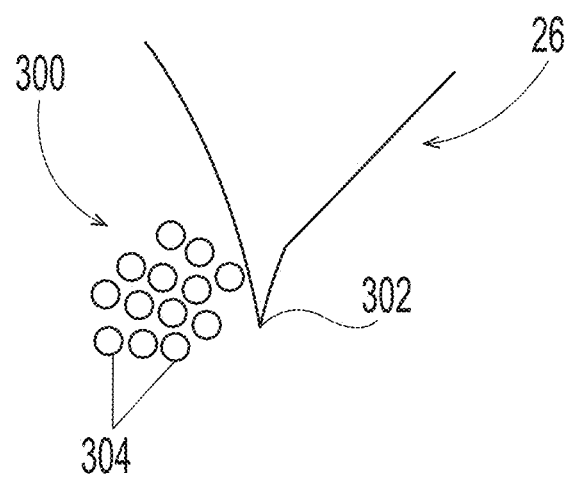
FIG. 33 is an example cross-sectional illustration of a point of an aperturing pin pushing an elastic strand to one side to avoid elastic strand breakage.
Figure 34:
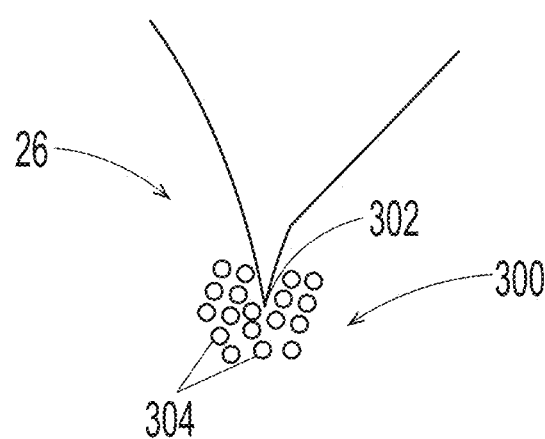
FIG. 34 is an example cross-sectional illustration of a point of an aperturing pin pushing some filaments of the elastic strand to one side and pushing other filaments of the elastic strand to another side to avoid full elastic strand breakage.

In some instances, it may be desirable to use elastic strands comprising multi-filament elastic strands. The elastic strands may be or may comprise Lycra® from Invista, Creora® from Hyosung, spandex, and/or elastane, for example. Mono-elastic strands may also be used such as Fullflex®, for example. Referring to FIG. 33, when the point 302 of the first distal ends 26 contacts a multi-filament elastic strand 300, or a single filament elastic strand, the point 302 may push the elastic strand 300 to one side or the other of the point 302 to avoid elastic strand breakage. In other instances, referring to FIG. 34, when the point 302 of the first distal ends 26 contacts a multi-filament elastic strand 300, the point 302 may push some of the filaments 304 of the elastic strand 300 to one side of the point 302 and push other portions of the filaments 304 to another side of the point 302. The point 302 may even break some of the filaments while leaving the overall elastic strand generally in-tact. In such a fashion, elastic strand breakage may be eliminated or reduced.

Figure 35:
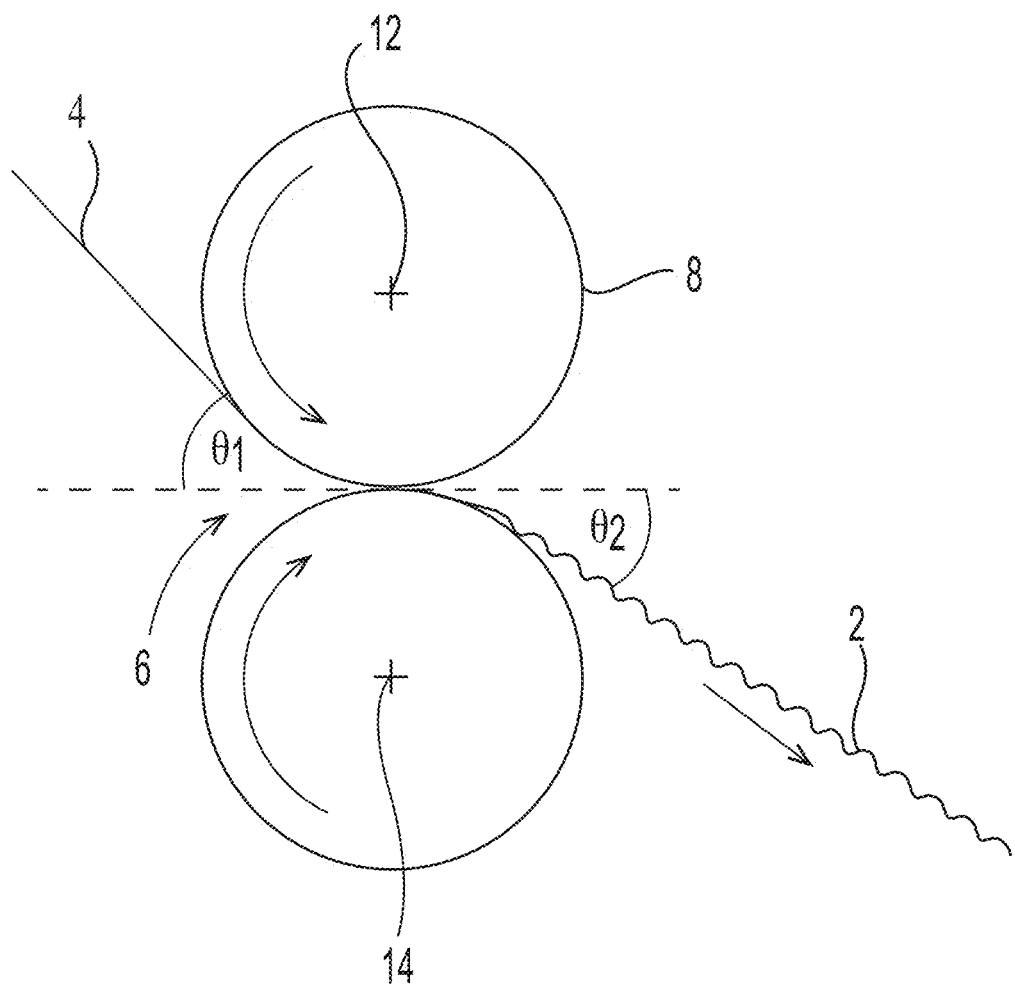
FIG. 35 is a schematic illustration of a substrate being conveyed into a nip formed between first and second rolls at an in-feed angle and being conveyed out of the nip at an out-feed angle.

Referring to FIG. 35, even though the substrates are shown being conveyed through the nip 6 formed between the first and second rolls 8, 10 herein, it should be understood that the precursor substrates 4 may, in some instances, be conveyed into the nip 6 at an in-feed angle $\theta_1$ and/or the formed substrates 2 may be conveyed out of the nip at an out-feed angle $\theta_2$. The in-feed angle $\theta_1$ and the out-feed angle $\theta_2$ may be in the range of about 2 degrees to about 50 degrees, about 5 degrees to about 40 degrees, or about 5 degrees to about 30 degrees, specifically reciting all 0.5 degree increments within the above-specified ranges and all ranges formed therein or thereby. In the example of FIG. 35, the first roll 8 is configured to create apertures in the substrates and the second roll 10 is configured creates three-dimensional elements in the substrates. Conveying the substrates 4 toward the nip 6 at an in-feed angle $\theta_1$ may help lock the substrate 4 to the first roll 8 prior to the substrate entering the nip 6 owing to the substrates 4 being pierced by the points of the first distal ends 26. This locking of the substrates 4 may help three-dimensional element formation in or proximate to the nip 6. If the first roll 8 is heated, conveying the substrate at an in-feed angle $\theta_1$ may also be desired to allow for adequate heat transfer to occur between the first roll 8 and the substrates. Conveying the substrates 2 out of the nip 6 at an out-feed angle $\theta_2$ may be desired to fully form and "set" the three-dimensional elements in the substrates 2 and to transfer adequate heat from the second roll 10 to the substrates 2, again to aid in three-dimensional element formation.

The elastic strands may be joined to the one or more nonwoven substrates using mechanical entrapment, such as by using thermal welds or bonds, and/or by using adhesives, to form the elastic belts. When adhesives are used to join the elastic strands to the nonwoven substrates to form the elastic belts, adhesives may contaminate the roll, such as rolls 8, 10 herein. This contamination may be caused by the adhesive being forced through pores in the elastic belts owing to tight clearances and pressure formed in the nip between the rolls 8, 10. It may be difficult to clean the rolls during manufacturing. As such, the present inventors have discovered methods of reducing roll contamination by the adhesives. First, the rolls may be heated. By heating the rolls, any adhesive on the rolls may remain hot or warm, and thereby be less sticky or tacky. Second, the rolls may be cooled to the point where condensate water may collect on the rolls, thereby resisting the adhesive from sticking to the rolls. Third, an oil, such as a mineral or silicone oil, for example may be applied to the rolls to prevent, or at least inhibit, the adhesive from sticking to the rolls. This oil may be applied to the rolls via a felt roller or sprayed onto the rolls, for example. Fourth, a surface coating, such as a plasma coat or Teflon® comprising coating, may be applied to the rolls, to prevent, or at least inhibit, the adhesive from sticking to the rolls. Other methods of preventing, or at least inhibiting the adhesive from sticking to the rolls are also within the scope of the present disclosure.

Methods

Methods of making elastic belts, especially three-dimensional, apertured elastic belts are now discussed. A method of making a three-dimensional, apertured elastic belt for an absorbent article may comprise conveying an elastic belt in a machine direction. The elastic belt may comprise a first nonwoven substrate, at least a second nonwoven substrate, and a plurality of elastic strands positioned intermediate the first nonwoven substrate and the second nonwoven substrate. The elastic strands may comprise a plurality of filaments. The elastic strands may be strained in the machine direction. The method may comprise providing a first roll having a first rotational axis and providing a second roll having a second rotational axis. The first rotational axis and the second rotational axis may be positioned generally parallel to each other to form a nip between the first and second roll. The method may comprise rotating the first roll in a first direction about the first rotational axis and rotating the second roll in a second, opposite direction about the second rotational axis. The method may comprise forming apertures in the elastic belt in or proximate to the nip using the first roll and the second roll. The method may comprise forming three-dimensional elements in the elastic belt in or proximate to the nip in areas free of the apertures using the first roll and the second roll. The method may comprise forming compressed regions in the nip in the three-dimensional elements or around the apertures using the first roll and the second roll.

The first roll may comprise a first radial outer surface and a first plurality of projections extending at least partially outwardly from the first radial outer surface. The first plurality of projections may be configured to form the apertures in the elastic belt. The first roll may comprise a first plurality of recesses defined in the first radial outer surface and first distal portions of at least some of the first plurality of projections forming elongated aperturing structures. The elongated aperturing structures may comprise side walls. The first distal ends of at least some of the first plurality of projections may form a point.

The second roll may comprise a brush roll. In other forms, the second roll may comprise a felt roll. In still other forms, the second roll may comprise a solid material, such as steel (or other materials discussed herein), and may comprise a second radial outer surface and a second plurality of projections extending at least partially outwardly from the second radial outer surface. The second plurality of projections may or may not be configured to form the three-dimensional elements in the elastic belt. The second plurality of projections may comprise second distal portions and second distal ends. The second roll may comprise a second plurality of recesses defined in the second radial outer surface. At least some of the second distal portions may comprise shoulders.

The method may comprise intermeshingly engaging portions of the first plurality of projections with portions of the second plurality of recesses in the nip and intermeshingly engaging portions of the second plurality of projections with portions of the first plurality of recesses in the nip. The method may comprise compressing the elastic belt intermediate the side walls of the elongated aperturing structures and the shoulders of the second distal portions to form the compressed regions in the nip between the first and second rolls.

The elastic belt may be heated prior to the elastic belt being conveyed through the nip. The first and/or second rolls may be heated prior to the elastic belt being conveyed through the nip. The elastic belt may be heated in or proximate to the nip. The heating of the elastic belt may also be similar to the nonwoven substrates described herein.

Apertures formed in the elastic belts may have an area in the range of about 0.25 $mm^2$ to about 10 $mm^2$, about 0.3 $mm^2$ to about 8 $mm^2$, about 0.4 $mm^2$ to about 7 $mm^2$, about 0.4 $mm^2$ to about 5 $mm^2$, about 0.5 $mm^2$ to about 4 $mm^2$, or about 0.5 $mm^2$ to about 3 $mm^2$, specifically reciting all 0.1 $mm^2$ increments within the specified ranges and all ranges formed therein or thereby. The apertures may be pin apertured and may be generally circular or ovate. Apertures may be designed to be circular, but may be somewhat elongated into ovate shapes in the machine direction owing to manufacturing speeds.

The method may comprise conveying the elastic belt toward the nip at an in-feed angle, wherein the in-feed angle is not zero. The method may comprise conveying the elastic belt out of the nip at an out-feed angle, wherein the out-feed angle is not zero.

A method of forming absorbent articles on an absorbent article manufacturing line may comprise providing an elastic belt. The elastic belt may comprise a first nonwoven substrate, at least a second nonwoven substrate, and a plurality of elastic strands positioned intermediate the first nonwoven substrate and the second nonwoven substrate. The plurality of elastic strands may be generally oriented in a machine direction. The elastic strands may comprise a plurality of filaments. The first nonwoven substrate has a first cross-directional width (relative to the machine direction arrow in FIG. 24). The second nonwoven substrate has a second cross-directional width (relative to the machine direction arrow in FIG. 24). The first cross-directional width may be larger than the second cross-directional width. The method may comprise conveying the elastic belt in the machine direction on the absorbent article manufacturing line. The elastic strands may be strained in the machine direction (see FIG. 24 for machine direction). The method may comprise attaching a portion of an absorbent article chassis to a portion of the second nonwoven substrate and folding a portion of the first nonwoven substrate that extends beyond the second nonwoven substrate in the cross-machine direction over a portion of the second nonwoven substrate to create a fold over region. The method may comprise aperturing the elastic belt in areas within the fold over region and areas outside of the fold over region, but not in areas of overlap between the elastic belt and the portion of the absorbent article chassis.

The aperturing step may comprise providing a first roll having a first rotational axis and providing a second roll having a second rotational axis. The first rotational axis and the second rotational axis are positioned generally parallel to each other to form a nip between the first and second rolls. The aperture step may comprise rotating the first roll in a first direction about the first rotational axis, rotating the second roll in a second, opposite direction about the second rotational axis, and forming the apertures in the elastic belt in or proximate to the nip using the first and second rolls.

The method may comprise forming three-dimensional elements in the elastic belt in or proximate to the nip in areas free of the apertures using the first and second rolls. The method may comprise forming compressed regions in the nip in the three-dimensional elements or around the apertures using the first and second rolls.

The first roll may comprise a first radial outer surface and a first plurality of projections extending at least partially outwardly from the first radial outer surface. The first plurality of projections are configured to form the apertures in the elastic belt. The first roll may comprise a first plurality of recesses defined in the first radial outer surface and first distal portions of at least some of the first plurality of projections forming elongated aperturing structures. The elongated aperturing structures comprise side walls. The first distal ends of the at least some of the first plurality of projections may form a point.

The second roll may comprise a brush roll or a felt roll. The second roll may also comprise a roll formed of steel, or other materials disclosed herein. The second roll, for example a steel roll, may comprise a second radial outer surface and a second plurality of projections extending at least partially outwardly from the second radial outer surface. The second plurality of projections may be configured to form the three-dimensional elements in the elastic belt. The second plurality of projections may comprise second distal portions and second distal ends. The second roll may comprise a second plurality of recesses defined in the second radial outer surface. At least some of the second distal portions may comprise shoulders.

The method may comprise intermeshingly engaging portions of the first plurality of projections with portions of the second plurality of recesses in the nip and intermeshingly engaging portions of the second plurality of projections with portions of the first plurality of recesses in the nip.

The method may comprise compressing the elastic belt intermediate the side walls of the elongated aperturing structures and the shoulders of the second distal portions to form the compressed regions.

The elastic belt may be heated prior to the elastic belt being conveyed through the nip. The first and/or second rolls may be heated prior to the elastic belt being conveyed through the nip. The elastic belt may be heated in or proximate to the nip. The heating of the elastic belt may also be similar to the nonwoven substrates described herein.

Apertures formed in the elastic belts may have an area in the range of about 0.25 $mm^2$ to about 10 $mm^2$, about 0.3 $mm^2$ to about 8 $mm^2$, about 0.4 $mm^2$ to about 7 $mm^2$, about 0.4 $mm^2$ to about 5 $mm^2$, about 0.5 $mm^2$ to about 4 $mm^2$, or about 0.5 $mm^2$ to about 3 $mm^2$, specifically reciting all 0.1 $mm^2$ increments within the specified ranges and all ranges formed therein or thereby. The apertures may be pin apertured and may be generally circular or ovate. Apertures may be designed to be circular, but may be somewhat elongated into ovate shapes in the machine direction owing to manufacturing speeds.

The fold over region may not overlap the portion of the chassis attached to the second nonwoven substrate. The folding step may occur before or after the attaching step.

The method may comprise conveying the elastic belt toward the nip at an in-feed angle, wherein the in-feed angle is not zero. The method may comprise conveying the elastic belt out of the nip at an out-feed angle, wherein the out-feed angle is not zero.

A method of forming absorbent articles on an absorbent article manufacturing line is provided. The method may comprise providing an elastic belt (or more than one elastic belt), wherein the elastic belt may comprise a first nonwoven substrate, a second nonwoven substrate, and a plurality elastic strands positioned intermediate the first nonwoven substrate and the second nonwoven substrate. The plurality of elastic strands may be generally oriented in a machine direction. The method may comprise conveying the elastic belt in the machine direction on the absorbent article manufacturing line. The elastic strands may be strained in the machine direction. The method may comprise aperturing the elastic belt and, after the aperturing step, attaching a portion of an absorbent article chassis to a portion of the second nonwoven substrate. The absorbent article chassis may comprise a topsheet, a backsheet, and an absorbent core disposed between the topsheet and the backsheet.

A method of forming absorbent articles on an absorbent article manufacturing line is provided. The method may comprise providing an elastic belt (or more than one elastic belt), wherein the elastic belt may comprise a first nonwoven substrate, a second nonwoven substrate, and a plurality elastic strands positioned intermediate the first nonwoven substrate and the second nonwoven substrate. The plurality of elastic strands may be generally oriented in a machine direction. The first nonwoven substrate may have a first cross-directional width. The second nonwoven substrate may have a second cross-directional width. The first cross-directional width may be larger than the second cross-directional width. The method may comprise conveying the elastic belt in the machine direction on the absorbent article manufacturing line. The elastic strands may be strained in the machine direction. The method may comprise folding a portion of the first nonwoven substrate that extends beyond the second nonwoven substrate in the cross-machine direction over a portion of the second nonwoven substrate to create a fold over region. The method may comprise aperturing the elastic belt in areas within the fold over region and areas outside of the fold over region. The method may comprise, after the aperturing step, attaching a portion of an absorbent article chassis to a portion of the second nonwoven substrate. The absorbent article chassis may comprise a topsheet, a backsheet, and an absorbent core disposed at least partially intermediate the topsheet and the backsheet.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. A method of forming absorbent articles on an absorbent article manufacturing line, the method comprising:
   providing an elastic belt, wherein the elastic belt comprises a first nonwoven substrate, a second nonwoven substrate, and a plurality elastic strands positioned intermediate the first nonwoven substrate and the second nonwoven substrate, wherein the plurality of elastic strands are generally oriented in a machine direction, wherein the first nonwoven substrate has a first cross-directional width, wherein the second nonwoven substrate has a second cross-directional width, and wherein the first cross-directional width is larger than the second cross-directional width;
   conveying the elastic belt in the machine direction on the absorbent article manufacturing line, wherein the elastic strands are strained in the machine direction;
   attaching a portion of an absorbent article chassis to a portion of the second nonwoven substrate, wherein the absorbent article chassis comprises a topsheet, a backsheet, and an absorbent core disposed at least partially intermediate the topsheet and the backsheet;
   folding a portion of the first nonwoven substrate that extends beyond the second nonwoven substrate in the cross-machine direction over a portion of the second nonwoven substrate to create a fold over region;
   forming apertures through the elastic belt in areas within the fold over region and areas outside of the fold over region, but not in areas of overlap between the elastic belt and the absorbent core of the absorbent article chassis; and
   forming compressed regions in a nip.

2. The method of claim 1, wherein the elastic strands comprise a plurality of filaments.

3. The method of claim 1, comprising forming three-dimensional elements in the elastic belt, wherein the three-dimensional elements are free of the apertures.

4. The method of claim 3, wherein the three-dimensional elements are dome-shaped.

5. The method of claim 3, wherein the three-dimensional elements comprise side walls that are continuous.

* * * * *